United States Patent
Helfet et al.

(10) Patent No.: US 11,690,658 B2
(45) Date of Patent: Jul. 4, 2023

(54) PATELLA BONE PLATE AND METHODS OF FIXATION

(71) Applicant: DePuy Synthes Products, Inc., Raynham, MA (US)

(72) Inventors: David L. Helfet, New York, NY (US); Dean G. Lorich, New York, NY (US)

(73) Assignee: DePuy Synthes Products, Inc., Raynham, MA (US)

( * ) Notice: Subject to any disclaimer, the term of this patent is extended or adjusted under 35 U.S.C. 154(b) by 168 days.

(21) Appl. No.: 17/142,543

(22) Filed: Jan. 6, 2021

(65) Prior Publication Data
US 2021/0121214 A1    Apr. 29, 2021

Related U.S. Application Data

(62) Division of application No. 15/257,220, filed on Sep. 6, 2016, now Pat. No. 10,905,478.

(60) Provisional application No. 62/214,827, filed on Sep. 4, 2015.

(51) Int. Cl.
| | | |
|---|---|---|
| A61B 17/80 | (2006.01) | |
| A61B 17/56 | (2006.01) | |
| A61B 17/88 | (2006.01) | |
| A61B 17/84 | (2006.01) | |

(52) U.S. Cl.
CPC ...... *A61B 17/8061* (2013.01); *A61B 17/8085* (2013.01); *A61B 17/848* (2013.01); *A61B 17/8866* (2013.01); *A61B 2017/564* (2013.01)

(58) Field of Classification Search
CPC ............ A61B 17/8061; A61B 17/8071; A61B 17/8076; A61B 17/8085
See application file for complete search history.

(56) References Cited

U.S. PATENT DOCUMENTS

| | | |
|---|---|---|
| 4,240,162 A | 12/1980 | Devas |
| 5,139,497 A | 8/1992 | Tilghman et al. |
| 5,201,737 A | 4/1993 | Leibinger et al. |
| 5,578,036 A | 11/1996 | Stone et al. |
| 5,593,450 A | 1/1997 | Scott et al. |
| 5,690,631 A | 11/1997 | Duncan et al. |
| 5,718,705 A | 2/1998 | Sammarco |
| 5,743,913 A | 4/1998 | Wellisz |
| 5,785,712 A | 7/1998 | Runciman et al. |
| 5,814,048 A | 9/1998 | Morgan |

(Continued)

FOREIGN PATENT DOCUMENTS

| | | |
|---|---|---|
| CN | 202211744 U | 5/2012 |
| CN | 202446238 U | 9/2012 |

(Continued)

OTHER PUBLICATIONS

Arthrex, Stephan Winkler Illustrations, Anatomically Research/Medical, 2015, 7 pages.

(Continued)

*Primary Examiner* — Anu Ramana
(74) *Attorney, Agent, or Firm* — BakerHostetler

(57) ABSTRACT

A patella fracture fixation system includes a peripheral rim bone plate that is configured to be implanted along a parapatellar lateral approach. The bone plate can configured to minimize disruption of blood supply to the patella. The bone plate can be augmented with a Krackow suture pattern to assist in stabilization of a comminuted inferior pole.

15 Claims, 9 Drawing Sheets

(56) References Cited

U.S. PATENT DOCUMENTS

| | | | |
|---|---|---|---|
| 5,961,519 | A | 10/1999 | Bruce et al. |
| 6,093,188 | A | 7/2000 | Murray |
| 6,093,201 | A | 7/2000 | Cooper et al. |
| 6,221,075 | B1 | 4/2001 | Toermala et al. |
| RE37,249 | E | 6/2001 | Leibinger et al. |
| 6,348,052 | B1 | 2/2002 | Sammarco |
| 6,652,530 | B2 | 11/2003 | Ip et al. |
| 6,929,646 | B2 | 8/2005 | Gambale |
| 6,960,211 | B1 | 11/2005 | Pfefferle et al. |
| 7,220,263 | B2 | 5/2007 | Cordaro |
| 7,335,204 | B2 | 2/2008 | Tornier |
| 7,500,976 | B2 | 3/2009 | Suh |
| 7,740,634 | B2 | 6/2010 | Orbay et al. |
| D623,743 | S | 9/2010 | Den et al. |
| 7,963,979 | B2 | 6/2011 | Phillips et al. |
| 8,147,493 | B2 | 4/2012 | Dutoit et al. |
| 8,246,663 | B2 | 8/2012 | Lovald et al. |
| 8,257,403 | B2 | 9/2012 | Den et al. |
| 8,261,750 | B1 * | 9/2012 | Barry ............... A61B 17/56 128/898 |
| 8,298,292 | B2 | 10/2012 | Swords et al. |
| 8,343,196 | B2 | 1/2013 | Schneider |
| 8,372,123 | B2 | 2/2013 | Smisson et al. |
| 8,512,384 | B2 | 8/2013 | Beutter et al. |
| 8,551,143 | B2 | 10/2013 | Norris et al. |
| 8,728,126 | B2 | 5/2014 | Steffen |
| 8,808,334 | B2 | 8/2014 | Strnad et al. |
| 8,906,071 | B2 | 12/2014 | Norris et al. |
| 8,906,072 | B2 | 12/2014 | Norris et al. |
| 8,906,073 | B2 | 12/2014 | Norris et al. |
| 9,517,097 | B2 | 12/2016 | Rise et al. |
| 10,327,824 | B2 | 6/2019 | Ricker et al. |
| 10,765,462 | B2 | 9/2020 | Penman et al. |
| 11,039,868 | B2 | 6/2021 | Ricker et al. |
| 2004/0039395 | A1 * | 2/2004 | Coon ............... A61B 17/155 606/87 |
| 2004/0102775 | A1 | 5/2004 | Huebner |
| 2005/0261780 | A1 | 11/2005 | Heino et al. |
| 2006/0025772 | A1 | 2/2006 | Leibel et al. |
| 2008/0009872 | A1 | 1/2008 | Vaughen et al. |
| 2008/0119895 | A1 | 5/2008 | Manceau |
| 2009/0182383 | A1 | 7/2009 | Prybyla et al. |
| 2009/0204121 | A1 | 8/2009 | Cavallazzi et al. |
| 2013/0090694 | A1 | 4/2013 | Norris et al. |
| 2014/0058510 | A1 | 2/2014 | Appenzeller et al. |
| 2014/0316472 | A1 | 10/2014 | Rise et al. |
| 2017/0065315 | A1 | 3/2017 | Helfet et al. |
| 2017/0105775 | A1 | 4/2017 | Ricker et al. |
| 2019/0000516 | A1 | 1/2019 | Vickaryous |

FOREIGN PATENT DOCUMENTS

| | | |
|---|---|---|
| CN | 203074840 U | 7/2013 |
| CN | 203244448 U | 10/2013 |
| CN | 203935262 U | 11/2014 |
| CN | 204092147 U | 1/2015 |
| EP | 0520177 A1 | 12/1992 |
| EP | 0820730 B1 | 1/2002 |
| EP | 2030596 A1 | 3/2009 |
| EP | 2923676 A1 | 9/2015 |
| FR | 2706278 A1 | 12/1994 |
| GB | 2437492 A | 10/2007 |
| GB | 2471648 A | 1/2011 |
| WO | 2013/055858 A1 | 4/2013 |
| WO | 2017/066682 A1 | 4/2017 |

OTHER PUBLICATIONS

Carpenter JE, Kasman RA, Patel N, Lee ML, Goldstein SA Biomechanical evaluation of current patella fracture fixation techniques. J Orthop Trauma. 1997;11(5):351-356.

Gosal HS, Singh P, Field RE Clinical experience of patellar fracture fixation using metal wire or non-absorbable polyester—a study of 37 cases. Injury. 2001;32(2):129-135.

Matejcic A, Puljiz Z, Elabjer E, Bekavac-Beslin M, Ledinsky M. Multifragment fracture of the patellar apex: Basket plate osteosynthesis compared with partial patellectomy. Arch Orthop Trauma Surg. 2008;128(4):403-408.

Matejcic A, Smiljanic B, Bekavac-Beslin M, Ledinsky M, Puljiz Z. The basket plate in the osteosynthesis of comminuted fractures of distal pole of the patella. Injury, 2006;37(6):525-530.

Taylor BC, Mehta S, Castaneda J, French BG, Blanchard C. Plating of patella fractures: Techniques and outcomes. J Orthop Trauma. 2014;28(9):e231-5.

Thelen S, Betsch M, Schneppendahl J, et al. Fixation of multifragmentary patella fractures using a bilateral fixed-angle plate. Orthopedics. 2013;36(11):e1437-43.

Thelen S, Schneppendahl J, Baumgartner R, et al. Cyclic long-term loading of a bilateral fixed-angle plate in comparison with tension band wiring with K-wires or cannulated screws in transverse patella fractures. Knee Surg Sports Traumatol Arthrosc. 2013;21(2):311-317.

Thelen S, Schneppendahl J, Jo pen E, et al. Biomechanical cadaver testing of a fixed-angle plate in comparison to tension wiring and screw fixation in transverse patella fractures. Injury. 2012;43(8):1290-1295.

Tian et al., Cannulated Screw and Cable are Superior to Modified Tension Band in the Treatment of Transverse Patella Fractures, Ciin. Orthop. Relat. Res, 2011, 469:3429-3435.

Wendl et al., Frakturen der Kniescheibe, Trauma und Berufskrankheit, vol. 4, issue 1, Apr. 2002, 30-37 (with English abstract).

Wild M, Eichler C, Thelen S, Jungbluth P, Windolf J, Hakimi M. Fixed-angle plate osteosynthesis of the patella—an alternative to tension wiring? Clin Biomech (Bristol, Avon) 2010;25(4):341-347.

DePuy Synthes, Variable Angle LCP Mesh Plate 2.4/2.7. Part of the Variable Angle LCP Forefoot/Midfoot System 2.4/2.7., Surgical Technique, Sep. 2015, 32 pages.

Konigsee Implantate, Variabel winkelstabile Patella-Platte, Variable angle-stable Patella-plate, titan/Titanium, Aug. 2013, 16 pages (with translation).

Medartis, Orbital Plating System OPS 1.5, MODUS Midface, Surgical Technique, Jun. 2013, 12 pages.

Orthopedic Implant—Orthopedic Implants Exporter from Ahmedabad, Maxillofacial Implants plates, https://www.indiamart.com/uteshiyamedicare/orthopedic-implant.html, Aug. 3, 2017, 2 pages.

Vajapey et al., Contourable craniofacial mesh plate osteosynthesis of patellar fractures: A new, low-profile fixation technique, Journal of Clinical Orthopaedics and Trauma, 2019, 6 pages.

Wild et al., Fixed-Angle Plates in Patella Fractures—A Pilot Cadaver Study, European Journal of Medical Research, Jan. 2011 16:41-46.

* cited by examiner

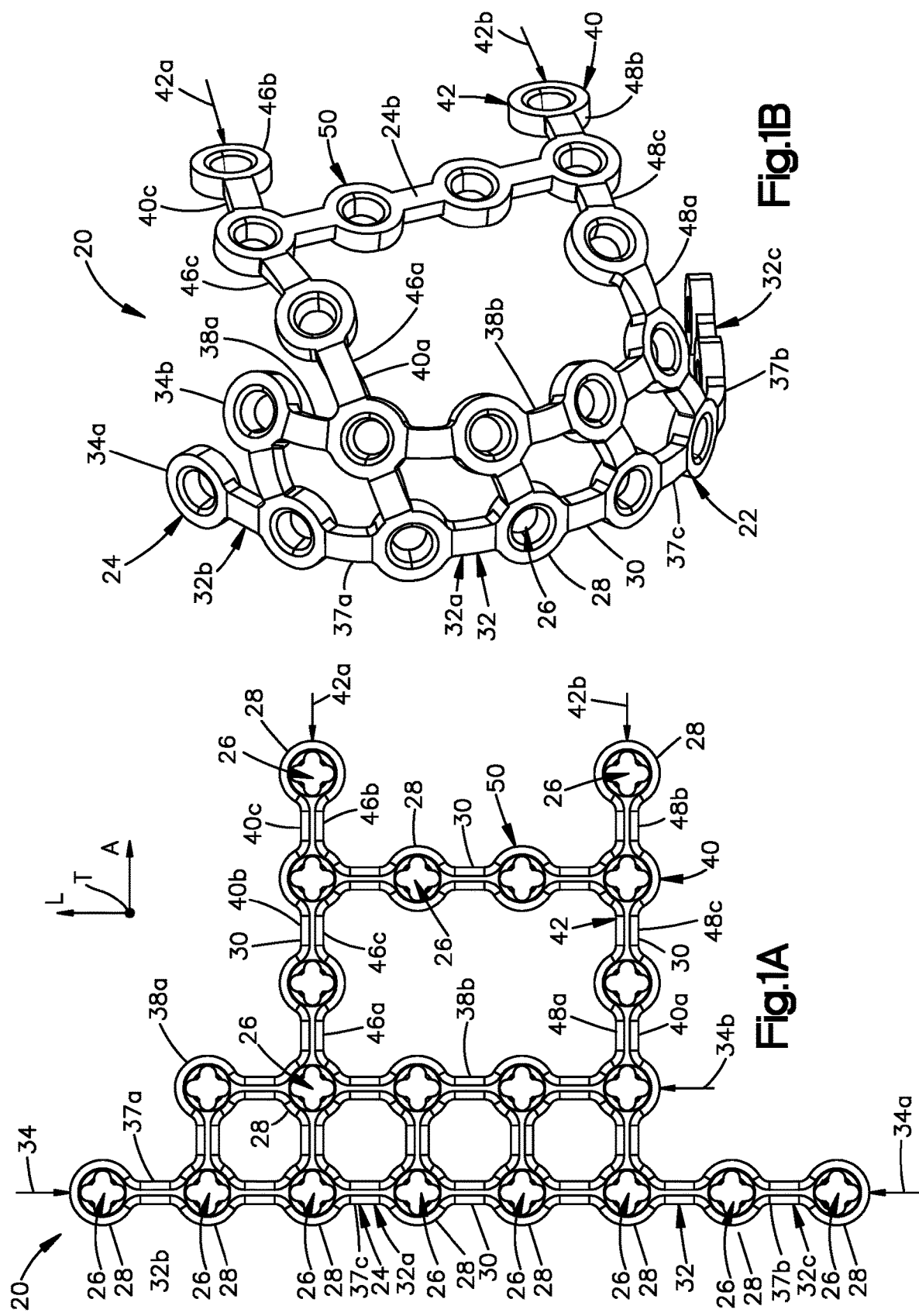

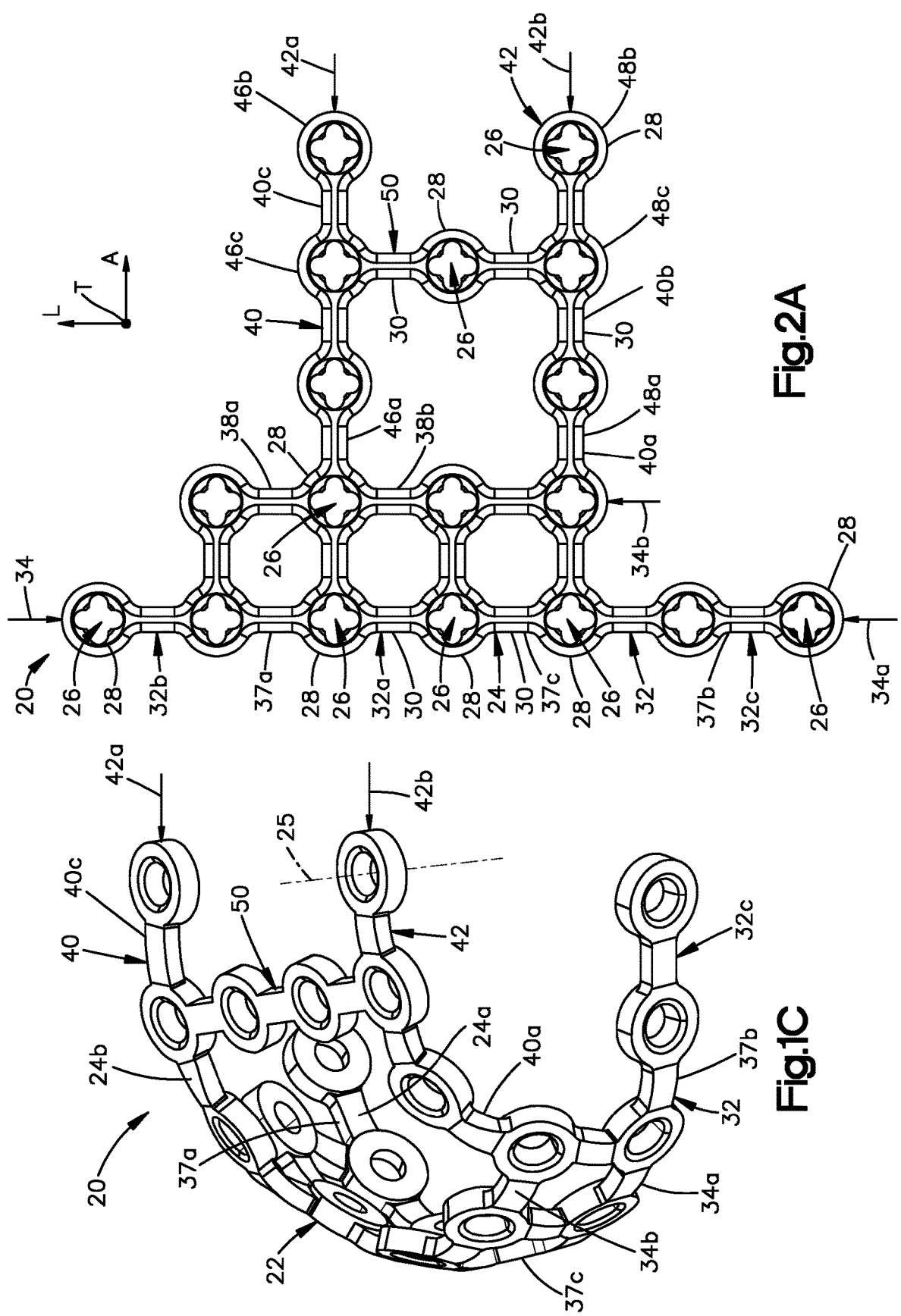

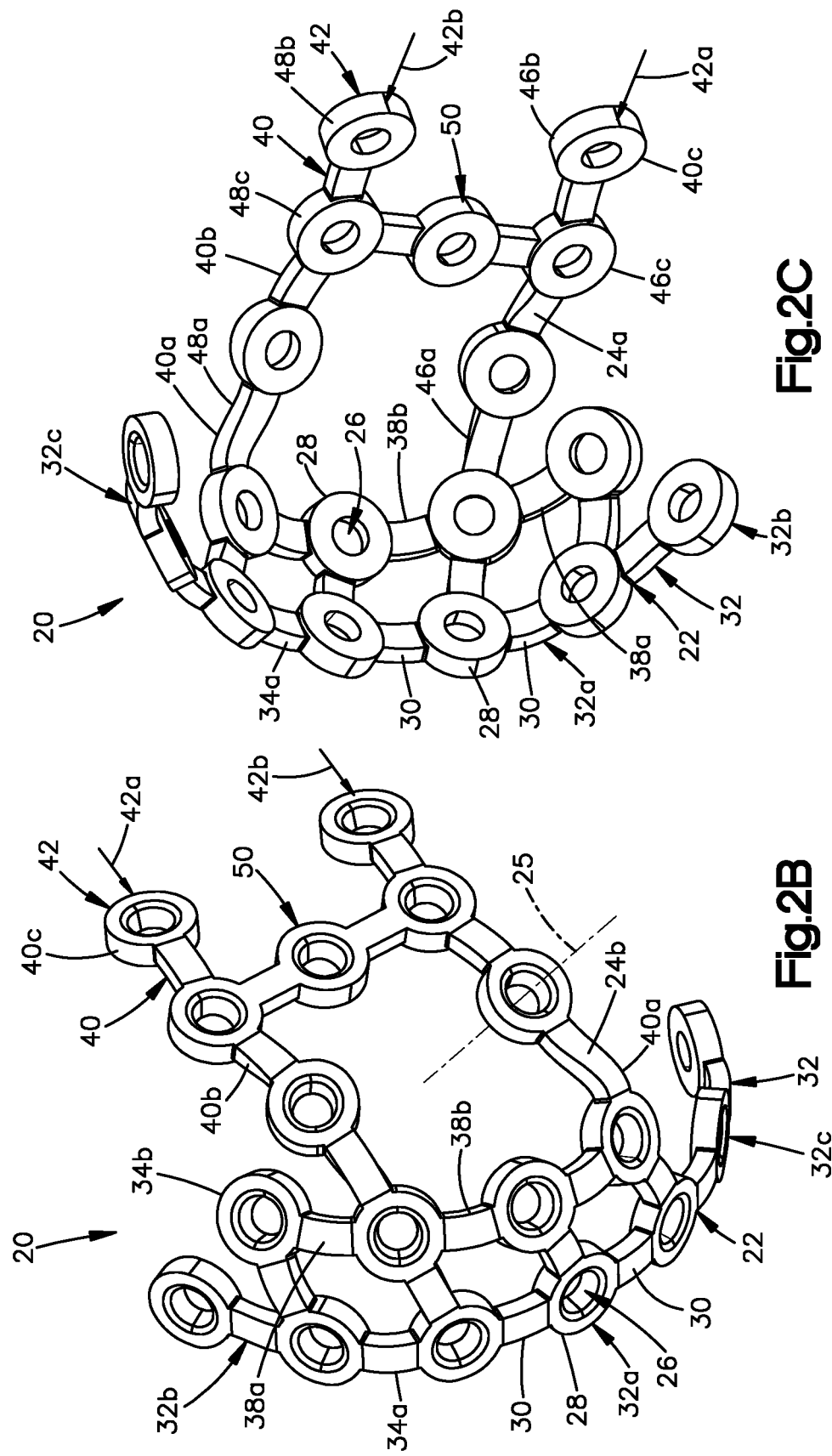

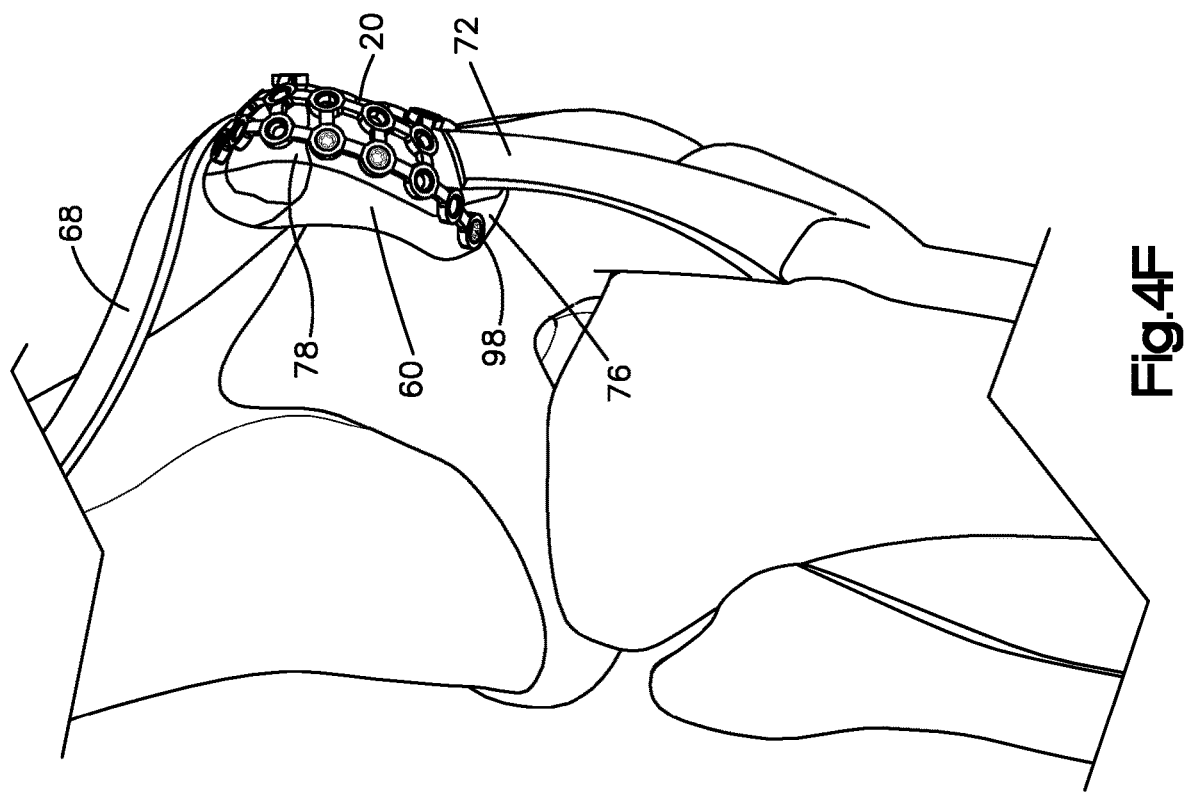
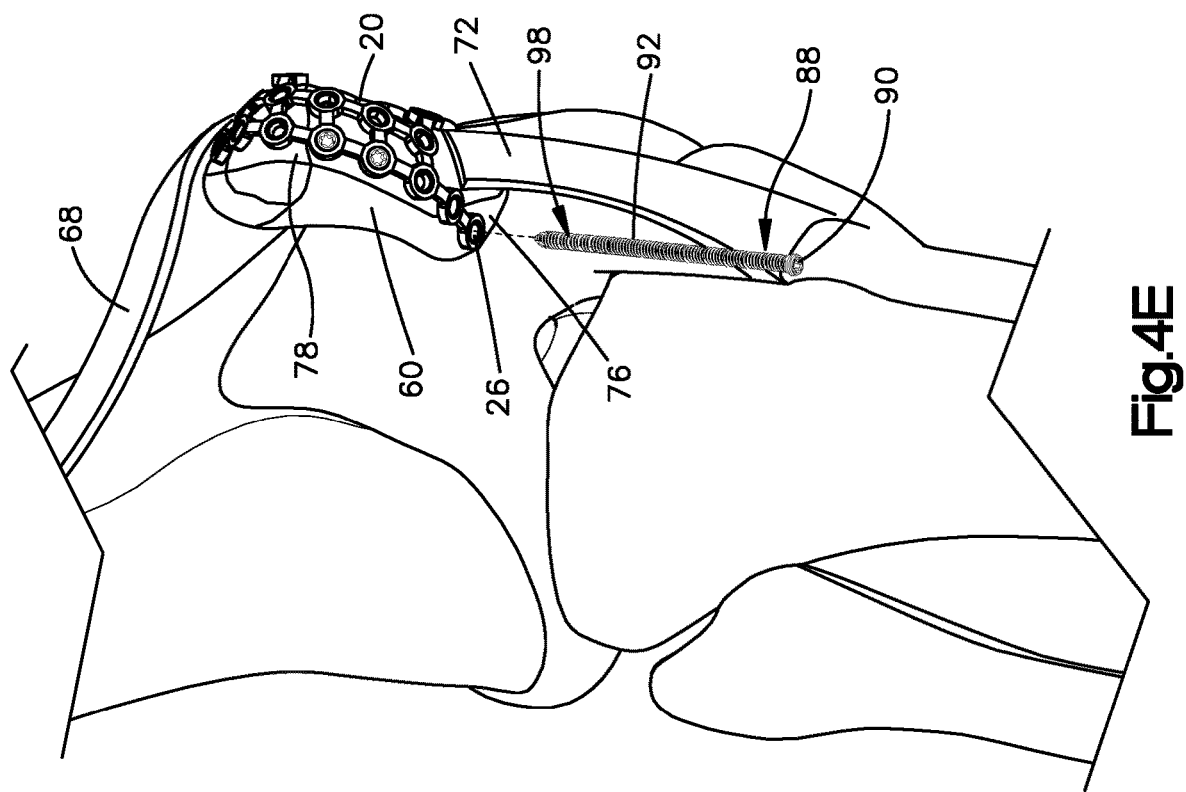

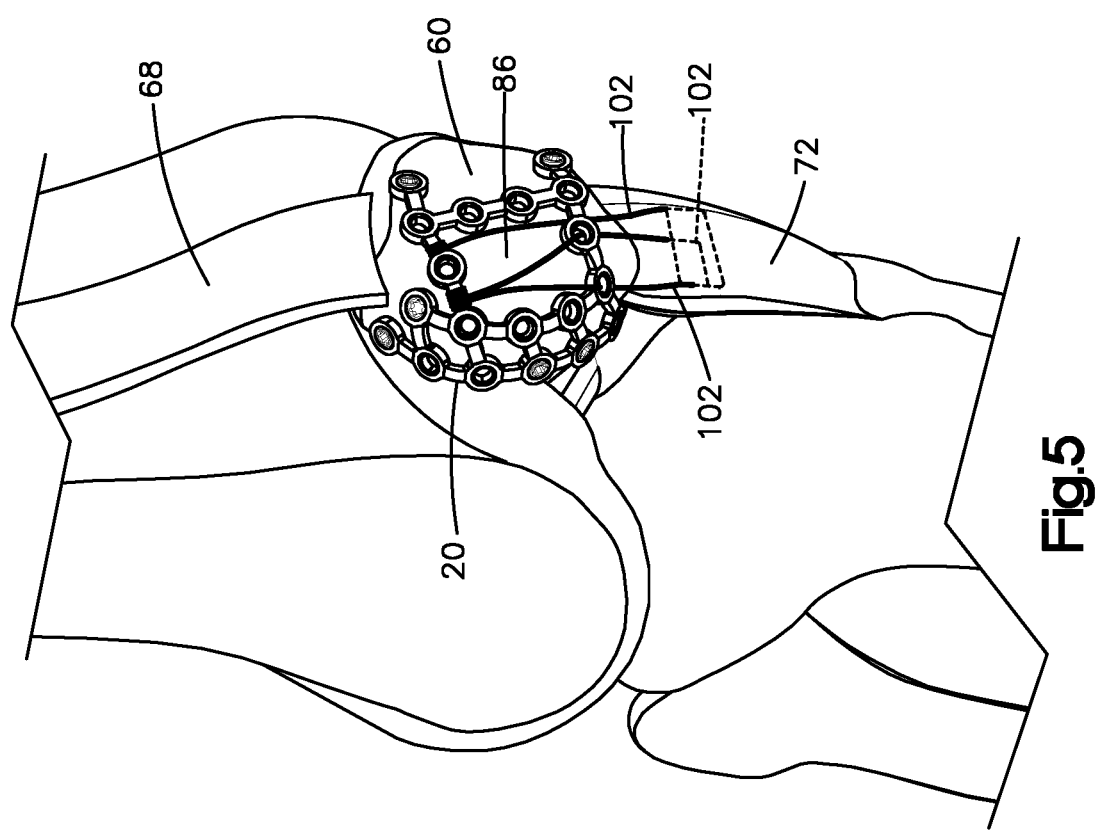

PATELLA BONE PLATE AND METHODS OF FIXATION

CROSS-REFERENCE TO RELATED APPLICATIONS

This is a divisional of U.S. patent application Ser. No. 15/257,220 filed Sep. 6, 2016, now U.S. Pat. No. 10,905,478, which in turn claims the benefit of U.S. Patent Application Ser. No. 62/214,827 filed Sep. 4, 2015, the disclosure of which is hereby incorporated by reference as if set forth in its entirety herein.

BACKGROUND

Patella fractures represent approximately 1% of all fractures and can be debilitating injuries resulting in extensor mechanism weakness, decreased knee range of motion, anterior knee pain, and degenerative patellofemoral arthritis. The limited soft tissue coverage and importance of the patella in knee extensor mechanism function has made operative treatment of these injuries challenging.

Historically, patellar fractures were treated non-operatively, which was thought to allow for adequate pain relief and partial restoration of extensor mechanism function. However, as surgical knowledge and technique has advanced, management of these injuries has evolved from non-operative care or patellectomy to anatomic reduction and internal fixation with a goal of osseous union.

Today, a non-operative treatment course can be recommended for non-displaced fractures of the patella, particularly when the fracture is non-displaced, the articular surface is not disrupted, and the extensor mechanism is intact. However, a disruption of the articular surface of as little as 2 mm or separation of bone fragments by as little as 3 mm is conventionally associated with an unacceptable risk of unsuitable bone healing. Additionally, patients with patella fractures often have concurrent retinacular tears that can result in fracture displacement and disruption of the extensor mechanism. Further, because of the important role of the patella in maintaining normal kinematics of the knee, operative management is considered to be the treatment of choice for patella fractures when patellar bone fragments are displaced, or the articular surface is disrupted.

One construct commonly used for the operative fixation of patella fractures is a tension band. In particular, an anterior tension band is applied by passing wires or braided cables or sutures behind previously implanted K-wires at the superior and inferior poles, crossing them, and twisting the ends to create a figure-eight pattern. Finally, a wire or braided cable is wrapped circumferentially around the patella directly on bone at a location anterior to the previously placed wires, and is tightened by twisting. A modification of this technique can be performed by replacing the K-wires with cannulated screws, such that a wire or braided cable or suture can be passed through the cannulated screws to create the anterior tension band with a figure-eight configuration, followed by application of a cerclage wire directly on the circumference of the patella.

While tension band constructs are the most common method of fixation, anterior knee pain, failure of the construct, and functional limitation with tension band fixation have all been reported. Further, this technique often fails to address inferior pole comminution commonly seen in fractures of the patella.

More recently, biomechanical studies have shown an advantage to fixation of patella fractures with plating constructs as opposed to tension band fixation. While various different patella plating constructs in use today can achieve satisfactory fracture reductions, the ultimate outcomes are often ineffective and clinically poor. In particular, despite reliable fracture healing and restoration of the extensor mechanisms, outcomes often remain unacceptable with convention techniques. A common misconception among surgeons is that patients recovering from patella fracture fixation mostly do well. However, this is likely because patients are not followed long enough post-operatively. Anterior knee pain after patellar fracture fixation is a common complaint during daily activity. Potential causes include patella baja, extensor mechanism malalignment, articular injury and posttraumatic arthritis, painful implants, or avascular necrosis. This anterior knee pain leads to limited rehabilitation and functional impairment.

Still another surgical option is to perform a partial or total patellectomy, though these procedures are typically reserved for extreme cases such as open injuries. Patellectomy procedures produce a high risk for creating patella baja, and bone-to-bone healing is preferred over tendon-to-bone healing. Also, a partial patellectomy procedure is likely to disrupt the main blood supply to the patella as it enters the inferior pole.

In other instances of an isolated inferior pole fracture that does not include the articular surface, fracture repairs are sometimes be performed with what are commonly known as Krackow sutures. In particular, Krackow sutures are placed on the medial and lateral aspects of the patellar tendon, and retrograde drill holes are created from the interior pole to the superior apex of the patella. The sutures are then passed through the drill holes and tied over the superior bony edge of the patella.

SUMMARY

In one aspect of the present disclosure, a bone plate is provided for fixation to a fractured patella. The bone plate can include a bone plate body that defines an inner surface configured to face the patella, and an outer surface opposite the inner surface. The bone plate body can include a base that is configured to surround a lateral portion of a circumferential rim of the patella. The base can include an intermediate section, a first outer section that extends substantially in a first select longitudinal direction from the intermediate section, and a second outer section that extends from the intermediate section substantially in a second select longitudinal direction opposite the first longitudinal direction. The bone plate body can further include an outer portion that extends from the base in a first select lateral direction substantially perpendicular to each of the first and second select longitudinal directions. Each of the intermediate section, the first outer section, the second outer section, and the outer portion can define a respective at least one bone fixation hole that extends through the bone plate body from the outer surface to the inner surface.

BRIEF DESCRIPTION OF THE DRAWINGS

The following detailed description will be better understood when read in conjunction with the appended drawings, in which there is shown in the drawings example embodiments for the purposes of illustration. It should be understood, however, that the present disclosure is not limited to the precise arrangements and instrumentalities shown. In the drawings:

FIG. 1A is a top plan view of a patella bone plate constructed in accordance with one embodiment, shown in a flat configuration;

FIG. 1B is a perspective view of the patella bone plate illustrated in FIG. 1A, shown in a contoured configuration;

FIG. 1C is another perspective view of the patella bone plate illustrated in FIG. 1B, shown in the contoured configuration;

FIG. 2A is a top plan view of a patella bone plate constructed in accordance with another embodiment, shown in a flat configuration;

FIG. 2B is a perspective view of the patella bone plate illustrated in FIG. 2A, shown in a contoured configuration;

FIG. 2C is another perspective view of the patella bone plate illustrated in FIG. 2B, shown in the contoured configuration;

FIG. 4E is a schematic perspective view of the knee illustrated in FIG. 4D, shown with the superior fixation element inserted through the bone plate and into the patella, and further showing an inferior fixation element aligned for insertion through the bone plate and into the patella;

FIG. 4F is a schematic perspective view of the knee illustrated in FIG. 4E, shown with the inferior fixation element inserted through the bone plate and into the patella;

FIG. 5 is a schematic perspective view of the knee illustrated in FIG. 4G, shown augmented with Krackow sutures attached to the patellar tendon and the bone plate.

DETAILED DESCRIPTION

Figure 3C:
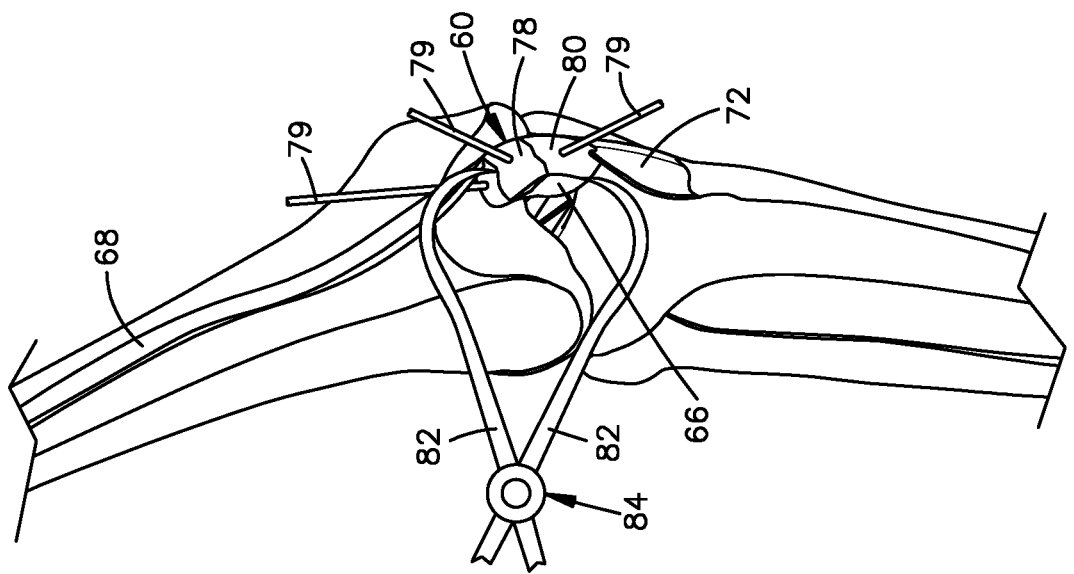
FIG. 3C is a schematic perspective view of the knee illustrated in FIG. 3B, shown after reduction of the bone fragments and angular articulation of the patella.

The present disclosure is related to a patella bone plate and methods of with fixing the bone plate to the patella. It has been discovered that the bone plate and associated methods of fixation provide for stability across multiple fracture fragments. The bone plate and associated methods can also address inferior pole comminution. Further, the bone plate can be fixed to the patella without compromising a vascular supply to the patella. The vascular supply that is avoided is currently believed to be the primary vascular supply to the patella.

A bone plate 20 will now be described with reference to FIGS. 1A-1C, it being appreciated that the description of the bone plate 20 illustrated in FIGS. 1A-1C also applies to the bone plate 20 illustrated in FIGS. 2A-2C unless otherwise indicated. The bone plate 20 is configured for fixation to the patella bone. In one example, the bone plate 20 can be configured as a mesh cage 22 that is configured to surround the lateral end of the circumferential or peripheral rim of the patella as well as a portion of the anterior cortex of the patella. Thus, as will be appreciated from the description below, the bone plate 20 is configured to provide fixation of a patella after fracture reduction so as to maintain alignment of the articular surface.

The bone plate 20 includes a bone plate body 24 that defines an inner surface 24a configured to face the patella, and an outer surface 24b opposite the inner surface 24a. The bone plate 20 further includes a plurality of fixation holes 26 that extend through the bone plate body 24 from the outer surface 24b to the inner surface 24a. In one example, the bone plate body 24 includes a plurality of eyelets 28 and links 30 that are connected between adjacent ones of the eyelets 28. The fixation holes 26 can extend through the eyelets 28 from the outer surface 24b to the inner surface 24a. In particular, the fixation holes 26 can extend through the eyelets 28 along respective central axes 25. One or more up to all of the links 30 can extend linearly from and to adjacent ones of the eyelets 28. Alternatively or additionally, one or more up to all of the links 30 can define bent regions between adjacent ones of the eyelets 28 so as to provide for linear distance adjustment between the corresponding adjacent ones of the eyelets 28. The links 30 and the eyelets 28 can be monolithic with each other. Alternatively, the links 30 and the eyelets 28 can be secured to each other using any attachment technique as desired. The bone plate 20 can be a titanium bone plate, a stainless steel bone plate, or any alternative suitable biocompatible made as desired that possesses the requisite strength for patella fixation.

As is described in more detail below with respect to FIGS. 4A-4G, the fixation holes 26 are configured to receive a respective fixation element that is configured for insertion through the fixation hole 26 and into the underlying patella so as to fix the bone plate 20 to the patella. Thus, a fixation system can include the bone plate 20 and the fixation elements. It should be appreciated, of course, that the bone plate 20 can be alternatively configured as desired so as to define the bone plate body and a plurality of fixation holes 26 that extend through the bone plate body 24 from the outer surface 24b to the inner surface 24a.

The plate body 24 can include any number of eyelets 28 as desired, it being appreciated that a greater number of eyelets allows for greater flexibility in the positioning of fixation elements to be driven into the patella. In this regard, it is recognized that patella fractures can be significantly comminuted, and that it may be desirable to drive the fixation elements into select ones of the bone fragments. By including a large number of eyelets 28, the fixation element can be aligned with a desired bone fragment.

With continuing reference to FIGS. 1A-1C, the bone plate 20 has a length that extends along a longitudinal direction L, a height that extends along a lateral direction A that is oriented substantially perpendicular with respect to the longitudinal direction L, and a thickness that extends along a transverse direction T that is oriented substantially perpendicular to each of longitudinal direction L and the lateral direction A. Unless otherwise indicated, the longitudinal direction as used herein can include the longitudinal direction L and directions within 45 degrees of the longitudinal direction L. Similarly, unless otherwise indicated, the lateral direction as used herein can include the lateral direction A and directions within 45 degrees of the lateral direction A. Similarly, unless otherwise indicated, the transverse direction as used herein can include the transverse direction T and directions within 45 degrees of the transverse direction T.

When the bone plate 20 is in a flat configuration illustrated in FIG. 1A, the length and the height can be coplanar with each other. When the bone plate 20 is in a contoured configuration illustrated in FIGS. 1B-1C, the length and thus the longitudinal direction L can be curved in a first respective direction of curvature such that the inner surface 24a defines a concavity. Similarly, and the height and thus the lateral direction A can be curved in a second respective direction of curvature that is different than the first respective direction of curvature such that the inner surface 24a defines a concavity. The first and second directions of curvature can be substantially perpendicular to each other. In one example, the curvatures of the length and the height can be linear and thus can lie in respective first and second planes. The first and second planes can be substantially orthogonal to each other. In another example, the curvatures can be non-linear from eyelet to eyelet. It should thus be appreciated that the curvatures of the length and height can be shaped as desired such that the inner surface 24a is contoured to substantially match the contour of the patella.

The bone plate body 24, and thus the bone plate 20, can include a base 32 that extends along the longitudinal direction L. The base 32 is configured to attach to a peripheral rim of a patella, as will be described in more detail below. Thus, the bone plate can also be referred to as a patella peripheral rim bone plate. The bone plate body 24, and thus the bone plate 20, includes a plurality of bone fixation holes 26 that extend through the base 32 along the transverse direction T from the outer surface 24b to the inner surface 24a. For instance, the base 32 can include a plurality of eyelets 28 and links 30 connected between adjacent ones of the eyelets 28. In particular, the base 32 can include at least one row 34 of eyelets 28 that are spaced from each other along the longitudinal direction L. Thus, the at least one row 34 can be said to be oriented along the longitudinal direction L. The base 32 can define an intermediate section 32a, a first outer section 32b that extends out from a first side of the intermediate section 32a, and a second outer section 32c that extends out from a second side of the intermediate section 32a that is opposite the first side. Thus, the intermediate section 32a can be disposed between the first outer section 32b and the second outer section 32c. The first outer section 32b is configured to be fixed to the patella on the boney edge of the superior pole of the patella under (or posterior of) the quadriceps tendon. The second outer section 32b is configured to be secured to the non-articulating inferior pole of the patella under (or posterior of) the patellar tendon. Thus, the first outer section 32b can define a superior extension of the bone plate 20 when the bone plate 20 is configured and aligned for attachment to the patella. Similarly, the second outer section 32c can define an inferior extension of the bone plate when the bone plate 20 is configured and aligned for attachment to the patella.

The fixation holes 26 of the at least one row 34 can be at least partially aligned with each other along the longitudinal direction L. For instance, the fixation holes 26 of the at least one row 34 can be partially aligned with each other along the longitudinal direction L. In one example, the fixation holes 26 of the at least one row 34 can be aligned with each other along the longitudinal direction L. The central axes 25 of the fixation holes 26 that are said to be aligned along a direction can be inline with each other along that direction. Alternatively or additionally, the link 30 that is connected between the eyelets 28 of adjacent fixation holes 26 that are said to be aligned along a direction can extend along the direction from and to adjacent ones of the eyelets 28 that are said to be aligned with each other. Alternatively or additionally still, the link 30 that is connected between the eyelets 28 of adjacent fixation holes 26 that are said to be aligned along a direction can extend along the direction from and to adjacent ones of the eyelets 28 that are said to be aligned with each other. Alternatively or additionally still, the link 30 that is connected between the eyelets 28 of adjacent fixation holes 26 that are said to be aligned along a direction can extend from one location of a first one of the eyelets 28 at a first location, and can extend from a second location of a second one of the eyelets 28. The first and second locations can be aligned with each other along the direction.

Further, central axes 25 of the fixation holes 26 that are said to be at least partially aligned along one of the longitudinal direction L and the lateral direction A can be offset from each other along the other of the lateral direction A and the longitudinal direction L such that a plane defined by the transverse direction T and the one of the longitudinal direction L and the lateral direction A can pass through the fixation holes 26 of adjacent eyelets that are said to be partially aligned along the one of the longitudinal direction L and the lateral direction A. Alternatively or additionally, the link 30 that is connected between the eyelets 28 of adjacent fixation holes 26 that are said to be partially aligned along a direction can extend along a second direction that defines an angle with respect to the direction of partial alignment that is 45 degrees or less. Alternatively or additionally still, the link 30 that is connected between the eyelets 28 of adjacent fixation holes 26 that are said to be partially aligned along a direction can extend along a second direction that defines an angle with respect to the direction of partial alignment that is 45 degrees or less from and to adjacent ones of the eyelets 28 that are said to be partially aligned with each other. Alternatively or additionally still, the link 30 that is connected between the eyelets 28 of adjacent fixation holes 26 that are said to be partially aligned along a direction can extend from one location of a first one of the eyelets 28 at a first location, and can extend from a second location of a second one of the eyelets 28. The first and second locations can be aligned with each other along a second direction defines an angle with respect to the direction of partial alignment that is 45 degrees.

In one example, the at least one row 34 of the base 32 can include first and second rows 34a and 34b of eyelets 28, the rows spaced from each other along the lateral direction A. In this regard, the longitudinal direction L can define a row direction, and the lateral direction A can define a column direction. In one example, the second row 34b can be spaced from the first row 34a in a first select lateral direction. Thus, the first row 34a can be spaced from the second row in a second select lateral direction that is opposite the first select lateral direction. When the plate 20 is oriented and configured for fixation to the patella, the first select lateral direction can be defined by one or both of the anatomical medial direction and the anatomical anterior direction. Thus, the second row 34b can be spaced one or both of medially and anteriorly from the first row 34a when the bone plate 20 is configured and aligned for attachment to the patella.

The first and second rows 34a and 34b can be spaced from each other along the lateral direction A. The eyelets 28 of the first row 34a can be at least partially aligned with respective ones of the eyelets 28 of the second row 34b along the lateral direction A. For instance, the eyelets 28 of the first row 34a can be partially aligned with respective ones of the eyelets 28 of the second row 34b along the lateral direction A. In one example, the eyelets 28 of the first row 34a can be aligned with respective ones of the eyelets 28 of the second row 34b along the lateral direction A. In another example, the eyelets of the first and second row 34a and 34b can be staggered with respect to each other along the longitudinal direction L. The first and second rows 34a and 34b of eyelets can be oriented substantially parallel to each other. It is recognized that first and second rows 34a and 34b of eyelets 28 allow for positional flexibility along both the longitudinal direction L and the lateral direction A of bone fixation elements that pass through the eyelets 28 of the base 32 and into the anterior rim of the patella, as will be described in more detail below. Thus, the base 32 is configured to be fixed to the lateral rim of the patella at locations that are offset from each other both along the longitudinal direction L and the lateral direction A. For instance, selection of one of the first and second rows 34a and 34b allows for positional flexibility along the lateral direction A. Selection of one of the plurality of fixation holes 26 of a given one of the rows 34a and 34b allows for positional flexibility along the longitudinal direction L. Further, one or both of the rows 34a and 34b can be angulated along the superior and inferior portions of the rim of the patella so as to provide for additional positional flexibility along the lateral direction A.

The first and second rows 34a and 34b can include the same number of eyelets 28 or a different number of eyelets 28. In one example, the first row 34a has a greater number of eyelets than the second row 34b. The eyelets 28 of the first row 34a can be equidistantly spaced from each other along the longitudinal direction L a first distance. Further, the eyelets 28 of the second row 34b can be equidistantly spaced from each other along the longitudinal direction L a second distance. The second distance can be equal to the first distance. Alternatively, the second distance can be greater than or less than the first distance. The eyelets 28 of the second row 34b can be offset from the eyelets 28 of the first row 34a a respective distance along the lateral direction A that can be equal to one or both of the first and second distances. Alternatively, the eyelets 28 of the second row 34b can be offset from the eyelets 28 of the first row 34a a respective distance along the lateral direction A that can be different than each of the first and second distances.

The first row 34a can define a first longitudinal end 37a, a second longitudinal end 37b that is opposite the first longitudinal end 37a, and a middle segment 37c disposed between the first and second longitudinal ends 37a and 37b. The first longitudinal end 37a can be said to be spaced from the second longitudinal end 37b in a first select longitudinal direction. Similarly, the second longitudinal end 37b can be said to be spaced from the first longitudinal end 37a in a second select longitudinal direction opposite the first select longitudinal direction. The first longitudinal end 37a can be defined by the first outer section 32b. The second longitudinal end 37b can be defined by the second outer section 32c. The middle segment 37c can be defined by the intermediate section 32a. When the bone plate 20 is oriented and configured for fixation to the patella, the first select longitudinal direction can be at least partially defined by the superior direction. Thus, when the bone plate 20 is oriented and configured for fixation to the patella, the first select longitudinal direction can be at least partially defined by the inferior direction.

Similarly, the second row 34b can define a first longitudinal end 38a, and a second or middle segment 38b disposed adjacent the first longitudinal end 38a. It is also envisioned that the second row can include a second longitudinal end that is opposite the first longitudinal end 38a, such that the middle segment 38b disposed between the first longitudinal end 38a and the second longitudinal end. The first longitudinal end 38a can be spaced from the second longitudinal end in the first select longitudinal direction. The second longitudinal end can be spaced from the first longitudinal end 38a in the second select longitudinal direction. The first longitudinal end 38a can be defined by the first outer section 32b. The second longitudinal end can be defined by the second outer section 32c. The middle segment 38b can be defined by the intermediate section 32a.

The first row 34a defines a first longitudinal length from longitudinally outermost ends of the first row 34a. The second row 34b defines a second longitudinal length that can extend from longitudinally opposed outermost end of the second row 34b. The first longitudinal length can be greater than the second longitudinal length. Alternatively, the second longitudinal length can be greater than the first longitudinal length. Alternatively, the first longitudinal length can be substantially equal to the second longitudinal length. Accordingly, as will be appreciated from the description below, the first row 34a is configured to reach further around the superior and inferior poles of the patella than the second row 34b.

In one example, the first longitudinal end 37a of the first row 34a can be disposed outboard of the first longitudinal end 38a of the second row 34b along the longitudinal direction L, and in particular in the first select longitudinal direction. In particular, the first longitudinal end 37a can be offset from the first longitudinal end 38a a first offset distance. The second longitudinal end 37b of the first row 34a can be disposed outboard of the second row 34b along the longitudinal direction L, and in particular in the second select longitudinal direction. In particular, the second longitudinal end 37b can be offset from the second row 34b a second offset distance. In one example, the first offset distance can be less than the second offset distance. Thus, the first longitudinal end 37a can include fewer eyelets 28 than the second longitudinal end 37b that are disposed longitudinally outboard of the second row 34b. Alternatively, the first and second longitudinal ends 37a and 37b can include an equal number of eyelets 28 that are disposed longitudinally outboard of the second row 34b. Alternatively still, the second longitudinal end 37b can include fewer eyelets 28 than the first longitudinal end 37a that are disposed longitudinally outboard of the second row 34b. Thus, it should be appreciated, of course, that the first offset distance can be greater than the second offset distance. Alternatively still, the first offset distance can be substantially equal to the second offset distance.

It should be appreciated that while the base 32 has been described in accordance with one embodiment, and that numerous alternative designs are envisioned suitable for implantation as described in more detail below. For instance, while the base 32 has been described as including first and second rows 34a and 34b, the base 32 can include any number of rows as desired, greater than or equal to one. The first row 34a can define an outer boundary of the bone plate with respect to the second select lateral direction. It is further envisioned that the base 32 can be constructed without any rows but still including the first outer section 32b configured for fixation to the superior boney edge of the superior patella under (or posterior of) the quadriceps tendon, and the second outer section 32b configured to be secured to the non-articulating distal pole of the patella under (or posterior of) the patellar tendon.

With continuing reference to FIGS. 1A-1C, the bone plate body 24, and thus the bone plate 20, can further include an outer portion 40 that extends from the base 32 along the lateral direction A. The outer portion 40 can be monolithic with the base 32. Alternatively, the outer portion 40 can be fastened to the base 32 in any manner as desired. During use, when the base 32 surrounds a portion of the patella rim, the outer portion 40 is configured to extend medially over the anterior cortical surface of the patella. For instance, the base 32 can at least partially surround the lateral half of the patella rim. Thus, it should be appreciated that the base 32 can be contoured to fit against the patella rim, and the outer portion 40 can be contoured to fit against the anterior cortical surface of the patella. The bone plate body 24, and thus the bone plate 20 includes a plurality of bone fixation holes 26 that extend through the outer portion along the transverse direction from the outer surface 24b to the inner surface 24a. Thus, the patella peripheral rim bone plate 20 can be further configured to be fastened to the anterior surface of the patella.

For instance, the outer portion 40 can include a plurality of eyelets 28 and links 30 connected between adjacent ones of the eyelets 28. In particular, the outer portion 40 can include at least one column 42 of eyelets 28 that are spaced from each other along the lateral direction A. Thus, the at least one column 42 can be said to be oriented along the longitudinal direction A. The outer portion 40 can define an outer proximal end 40a, an outer intermediate section 40b, and an outer distal end 40c. The outer intermediate section 40b can be disposed between the outer proximal end 40a and the outer distal end 40c. The outer proximal end 40a can extend out from the base 32. The outer portion 40 can terminate at the outer distal end 40c which can be a free end. The outer portion 40 can thus be cantilevered from the base 32. The outer portion 40 is configured to be fixed to the patella at the anterior wall. In particular, the outer intermediate section 40b and the outer distal end 40c can be configured to receive fixation elements that extend through the anterior cortical surface and into the patella. Thus, the outer intermediate section 40b can extend medially from the outer proximal end 40a, and the outer distal end 40c can extend medially from the outer intermediate section 40b.

Whether the bone plate is in the flat configuration or the curved configuration, the base 32 can be elongate substantially along a first plane, and the outer portion 40 can extend from the base 32 substantially along a second plane, it being understood that each of the base 32 and the outer portion 40 can be contoured as desired to deviate from a plane. The first and second substantial planes can be substantially orthogonal with respect to each other.

The fixation holes 26 of the at least one column 42 can be at least partially aligned with each other along the longitudinal direction A. For instance, the fixation holes 26 of the at least one column 42 can be partially aligned with each other along the lateral direction A. In one example, the fixation holes 26 of the at least one column 42 can be aligned with each other along the lateral direction A.

In one example, the at least one column 42 of the outer portion 40 can include first and second limbs that extend out from the base 32. The first and second limbs can be defined by respective first and second columns 42a and 42b of eyelets 28, the columns spaced from each other along the longitudinal direction L. In one example, the first column 42a can be spaced from the second column 42b in the first select longitudinal direction. Thus, the second column 42b can be spaced from the first column 42a in the second select longitudinal direction. Thus, the first column 42a can be spaced superior with respect to the second column 42b when the bone plate 20 is oriented and configured for attachment to the patella.

The first and second columns 42a and 42b can be spaced from each other along the longitudinal direction L. The eyelets 28 of the first column 42a can be at least partially aligned with respective ones of the eyelets 28 of the second row 34b along the longitudinal direction L. For instance, the eyelets 28 of the first column 42a can be partially aligned with respective ones of the eyelets 28 of the second column 42b along the longitudinal direction L. In one example, the eyelets 28 of the first column 42a can be aligned with respective ones of the eyelets 28 of the second column 42b along the longitudinal direction L. In another example, the eyelets 28 of the first and second columns 42a and 42b can be staggered with respect to each other along the lateral direction A. The first and second columns 42a and 42b of eyelets 28 can be oriented substantially parallel to each other.

It is appreciated that first and second columns 42a and 42b of eyelets 28 allow for positional flexibility along both the longitudinal direction L and the lateral direction A of bone fixation elements that pass through the eyelets 28 of the base 32 and into the anterior wall of the patella, as will be described in more detail below. Thus, the outer portion 40 is configured to be fixed to the anterior wall of the patella at locations that are offset from each other both along the longitudinal direction L and the lateral direction A. In this regard, the first and second columns 42a and 42b can define first and second anterior extensions of the bone plate 20 when the bone plate 20 is configured and aligned for attachment to the patella 60. Thus, the outer portion 40 of the bone plate 20 can be referred to as an anterior portion of the bone plate 20 when the bone plate is aligned and configured for fixation to the patella.

Selection of one of the first and second columns 42a and 42b for fixation allows for positional flexibility along the longitudinal direction L. Selection of one of the plurality of fixation holes 26 of a given one of the columns 42a and 42b for fixation allows for positional flexibility along the lateral direction A. Further, one or both of the columns 42a and 42b can be angulated along the anterior wall so as to provide for additional positional flexibility along the longitudinal direction L. The application of the base 32 to the lateral half of the peripheral rim of the patella along with the fixation of the first and second columns 42a and 42b to the anterior wall of the patella permits fixation of the bone plate 20 to the patella in multiple planes of fixation.

The first column 42a can define a first lateral end 46a, a second lateral end 46b that is opposite the first lateral end 46a, and a middle segment 46c disposed between the first and second lateral ends 46a and 46b. The second lateral end 46b can be said to be spaced from the first lateral end 46a in the first select lateral direction. Similarly, the first lateral end 46a can be said to be spaced from the second lateral end 46b in the second select longitudinal direction. Thus, the second lateral end 46b can be spaced from the first lateral end 46a in at least the medial direction when the bone plate 20 is oriented and configured for fixation to the patella. The first lateral end 46a can be defined by the outer proximal end 40a. When the bone plate 20 is placed against the patella, the first lateral end 46a can extend anteriorly and medially, such that the first middle segment 46c and the second lateral end 46b can face the anterior surface of the patella. The second lateral end 46b can be defined by the second outer distal end 40c. The middle segment 46c can be defined by the outer intermediate section 40b.

Similarly, the second column 42b can define a first lateral end 48a, a second lateral end 48b that is opposite the first lateral end 48a, and a middle segment 48c disposed between the first lateral end 48a and the second lateral end 48b. The second lateral end 48b can be spaced from the first lateral end 48a in the first select lateral direction. The first lateral end 48a can be spaced from the second lateral end 48b in the second select lateral direction. The first lateral end 48a can be defined by the outer proximal end 40a. When the bone plate 20 is placed against the patella, the first lateral end 48a can extend anteriorly and medially, such that the first middle segment 48c and the second lateral end 48b can face the anterior surface of the patella. The second column 42b can be spaced from the first column 42a in the inferior direction. Thus, the first column 42a can be spaced from the second column 42b in the superior direction. The second lateral end 48b can be defined by the outer distal end 40c. The middle segment 48c can be defined by the outer intermediate section 40b.

The first column 42a defines a first lateral length from the first lateral end 46a to the second lateral end 46b. The second column 42b defines a second lateral length from the first lateral end 48a to the second lateral end 48b. The first lateral length can be substantially equal to the second lateral length. Thus, the second lateral ends 46b and 48b can be substantially aligned with each other along the longitudinal direction L. Alternatively, the first lateral length can be greater than the second length. Thus, the second lateral end 46b can be disposed laterally outboard, or medially during use, of the second lateral end 48b. Alternatively still, the first lateral length can be less than the second lateral length. Thus, the second lateral ends 48b can be disposed laterally outboard, or medially during use, of the second lateral end 46b. As will be appreciated from the description below, the first and second columns 42a and 42b are each configured to extend anteriorly from the base 32 to the anterior wall of the patella, and medially along the anterior wall of the patella.

The first and second columns 42a and 42b can include the same number of eyelets 28 or a different number of eyelets 28. The eyelets 28 of the first column 42a can be equidistantly spaced from each other along the lateral direction A a respective first distance. Further, the eyelets 28 of the second column 42b can be equidistantly spaced from each other along the lateral direction A a respective second distance. The respective second distance can be equal to the respective first distance. Alternatively, the respective second distance can be greater than or less than the respective first distance. Further still, the respective first and second distances defined by the eyelets 28 of the first and second columns 42a and 42b can be the same as or different than the first and second distances defined by the eyelets of the first and second rows 34a and 34b, respectively.

The eyelets 28 of the first column 42a can be offset from the eyelets 28 of the second column 42b a distance along the longitudinal direction L that can be greater than one or both of the respective first and second distances. Accordingly, the outer portion 40 can include at least one cross-beam 50 that extends between the first and second columns 42a and 42b, and is connected to each of the first and second columns 42a and 42b. The cross-beam 50 can be monolithic with one or both of the first and second columns 42a and 42b. Alternatively or additionally, the cross-beam 50 can be can be secured to one or both of the first and second columns 42a and 42b using any attachment technique as desired. The cross-beam 50 can include at least one eyelet 28, and first and second links 30 that are joined to the first and second columns 42a and 42b, respectively. In particular, one or both of the links 30 can be joined to respective eyelets 28 of the first and second columns 42a and 42b, respectively. The at least one eyelet 28 of the cross-beam 50 can be spaced from the eyelets 28 of the first and second columns 42a and 42b any distance along the longitudinal direction L as desired. In particular, the at least one eyelet 28 of the cross-beam 50 can be spaced from the eyelets 28 of the first and second columns 42a and 42b a distance along the longitudinal direction L can be the equal to or different than the respective first and second distances that the eyelets 28 of the first and second columns 42a and 42b are spaced from each other along the lateral direction A.

The outer distal end 40c of the outer portion 40 can be defined by the eyelets 28 of the outer portion 40 that are disposed outboard from the cross-beam in the first select lateral direction. Thus, the second lateral end 46b of the first column 42a can be defined by the at least one eyelet or eyelets 28 that are spaced from the cross-beam 50 in the first select lateral direction. The second lateral end 46b of the first column 42a can be defined by the at least one eyelet or eyelets 28 that are spaced from the cross-beam 50 in the first select lateral direction. The second lateral end 46b and 48b can include a single eyelet 28. Alternatively, the second lateral end 46b and 48b can include a plurality of eyelets 28 as desired.

The first and second outer sections 32b and 32c of the base 32, and thus the first and second longitudinal ends 37a and 37b of the first row 34a can be defined by those eyelets 28 of the first and second rows 34a and 34b that are disposed longitudinally outboard with respect to the eyelets 28 of the outer portion 40. For instance, the at least one eyelet 28 or eyelets 28 of the first longitudinal end 37a can be spaced from the outer portion 40 in the first select longitudinal direction. Thus, in one example, the at least one eyelet 28 or eyelets 28 of the first longitudinal end 37a can be spaced from the first column 42a in the first select longitudinal direction L. Similarly, the at least one eyelet 28 or eyelets 28 of the second longitudinal end 37b can be spaced from the outer portion 40 in the second select longitudinal direction. Thus, in one example, the at least one eyelet 28 or eyelets 28 of the second longitudinal end 37b can be spaced from the second column 42b in the second select longitudinal direction L.

Likewise, the first longitudinal end 38a of the second row 34b can be defined by those eyelets 28 of the second row 34b that are disposed longitudinally outboard with respect to the eyelets 28 of the outer portion 40 in the first select longitudinal direction. Thus, in one example, the at least one eyelet 28 or eyelets 28 of the first longitudinal end 38a can be spaced from the first column 42a in the first select longitudinal direction L. Similarly, if the second row 34b includes a second longitudinal lend 38b, the at least one eyelet 28 or eyelets 28 of the second longitudinal end 38b can be spaced from the outer portion 40 in the second select longitudinal direction. Thus, in one example, the at least one eyelet 28 or eyelets 28 of the second longitudinal end 38b can be spaced from the second column 42b in the second select longitudinal direction L.

It should be appreciated that while the outer portion 40 has been described in accordance with one embodiment, and that numerous alternative designs are envisioned suitable for implantation as described in more detail below. For instance, while the outer portion 40 has been described as including first and second rows columns 42a and 42b, the outer portion 40 can include any number of columns as desired, greater than or equal to one. The first column 42a can define an outer boundary of the outer portion 40 with respect to the first select longitudinal direction. The second column 42a can define an outer boundary of the outer portion 40 with respect to the second select longitudinal direction. Additional columns can be disposed between the first and second columns 42a and 42b with respect to the longitudinal direction.

Referring now to FIGS. 1A-1C and 2A-2C, the bone plate 20 can be provided in many different sizes as desired. In one non-limiting example, bone plates 20 having different longitudinal lengths are envisioned. As illustrated in FIGS. 1A-1C, the cross-beam 50 includes first and second eyelets 28 that are disposed between the first and second columns 42a and 42b. Further, the middle segment 37c of the first row 34a includes four eyelets 28. The middle segment 37c of the second row 34b also includes four eyelets. It is recognized, however, that the various segments of the bone plate 20 can include any number of eyelets 28 as desired. As illustrated in FIGS. 2A-2C, the cross-beam 50 includes a single eyelet 28 that is disposed between the first and second columns 42a and 42b. Further, the middle segment 37c of the first row 34a includes three eyelets 28. The middle segment 37c of the second row 34b also includes four three. It is recognized, however, that the various segments of the bone plate 20 can include any number of eyelets 28 as desired. It should be appreciated, however, that the intermediate section 32a of the base of a first bone plate 20 as illustrated in FIGS. 1A-1C can include a greater number eyelets 28 that extend along the longitudinal direction L compared to the eyelets 28 of the intermediate section 32a of a second bone plate 20 illustrated in FIGS. 2A-2C. Further, the cross-beam 50 of the first bone plate as illustrated in FIGS. 1A-1C can include a greater number of eyelets 28 that extend along the longitudinal direction L compared to the eyelets of the cross-beam 50 of the second bone plate of FIGS. 2A-2C.

Thus, it should be appreciated that the surgical provider can be provided with a kit of bone plates 20 of different sizes. The different sizes can be defined by the eyelets 28 as described above with respect to the bone plate 20 illustrated in FIGS. 1A-1C, and the bone plate 20 illustrated in FIGS. 2A-2C. It is recognized that the different sizes may be achieved in any suitable alternative manner as desired. Further still, the kit can include bone plates of different shapes suitable for implantation using the method described below. For instance, the base 32 can include a single row, or can include more than two rows. Further, the outer portion 40 can include one cross-beam or a plurality of cross-beams. Further still, the outer portion 40 can include more than two columns. The surgical provider can select the bone plate 20 deemed to be most suitable for the patella to which the bone plate 20 is to be affixed. The selection can be based at least in part on one or both of the size of the patella, and the shape of the patella.

Further, bone plates 20 can be provided to the surgical care provider as descried above with respect to either or both of FIGS. 1A-1C and FIGS. 2A-2C. Thus, the bone plate 20 can be pre-formed in the manner described above, so as to be contoured to the shape of a patella prior to being sent to the surgical provider. It is appreciated that the pre-sized and pre-shaped implant can be further cut and shaped by the surgical care provider to define contour that further fits the patella to which the bone plate 20 is to be affixed. It is envisioned that a pre-sized and pre-shaped implant is contoured so as to substantially fit the patient's patella prior to any cutting or manipulation by the surgical provider.

In an alternative embodiment, the surgical provider can be provided with a flat mesh sheet having an array of eyelets 28 that are spaced from each other along the row direction and the column direction, and connected to each other by the links 30 as described above. The mesh sheet can be cut to a shape described herein so as to define the bone plate 20, and contoured to the fractured patella to which the bone plate is to be fixed.

A method of fixation of the bone plate 20 to the patella to repair patella fractures will now be described. As will become appreciated from the description below, the bone plate 20 can provide a multiplanar fixation with the bone plate 20 that can provide a low profile fixation construct against the patella. The method of fixation can maintain anatomic reduction under direct visualization of complex articular injuries and of the articular reduction with compression plating and interfragmentary screw fixation, including inferior pole comminution, while minimizing or at least reducing disruption to the vascular supply to the patella compared to conventional plating techniques.

Figure 3B:
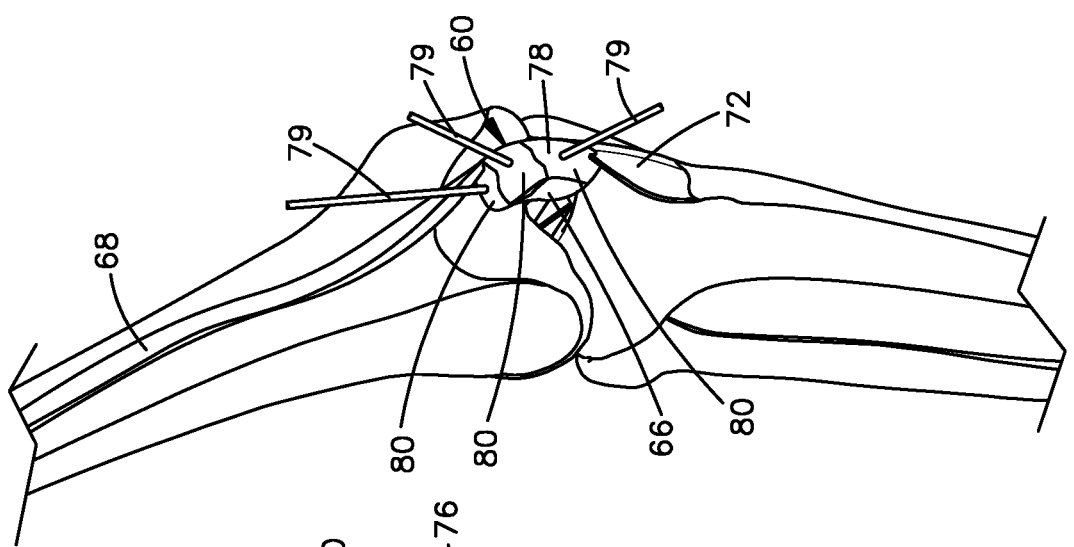
FIG. 3B is a schematic perspective view of the knee illustrated in FIG. 3A, shown after implantation of temporary fixation elements into bone fragments of the patella.
Figure 3A:
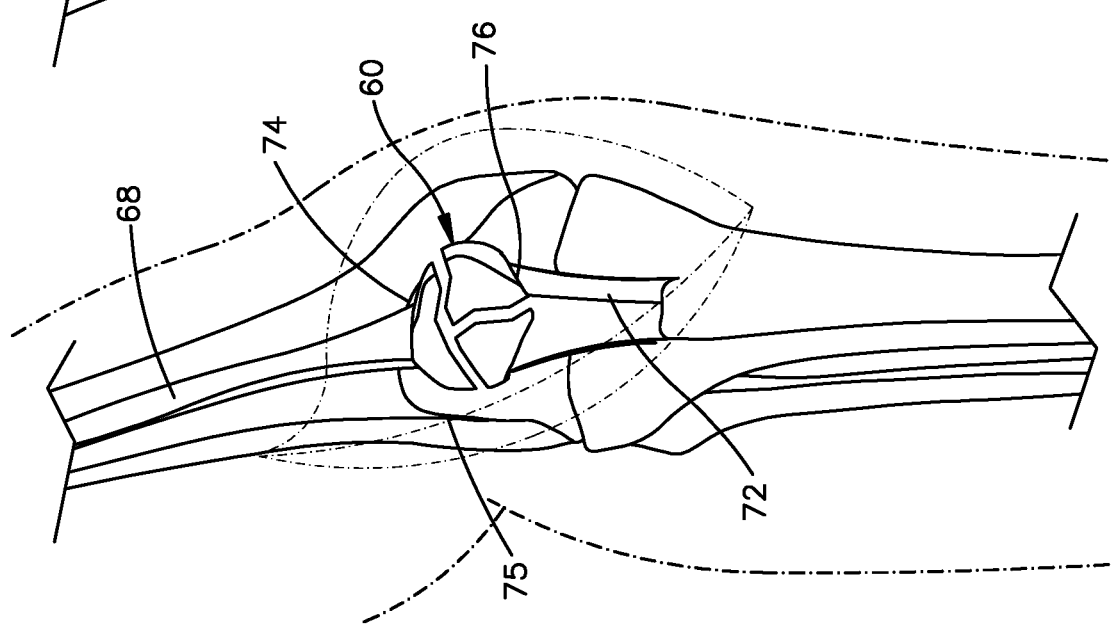
FIG. 3A is a schematic perspective view of a patient's knee, shown after a parapatellar lateral approach incision and completion of a parapatellar arthrotomy.
Figure 4A:
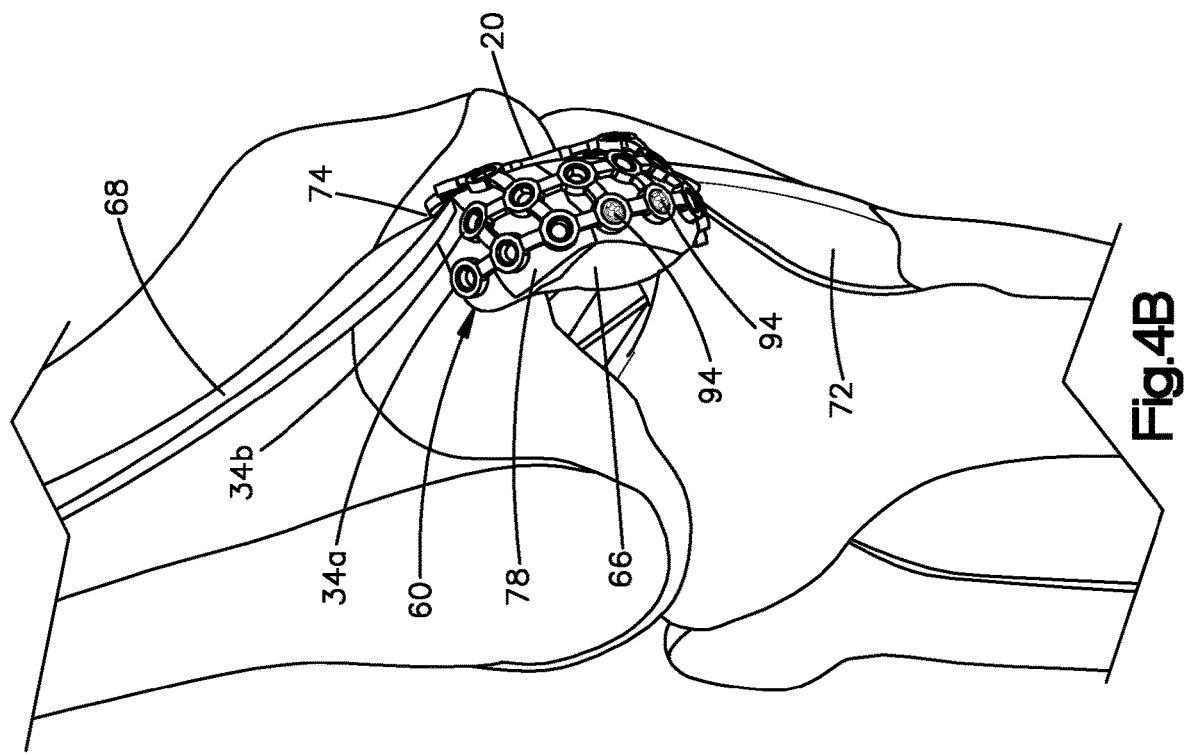
FIG. 4A is a schematic perspective view of the knee illustrated in FIG. 3C, showing placement of the bone plate illustrated in FIG. 1A against the patella, and lateral fixation elements aligned for insertion through the bone plate and into the patella.
Figure 4B:
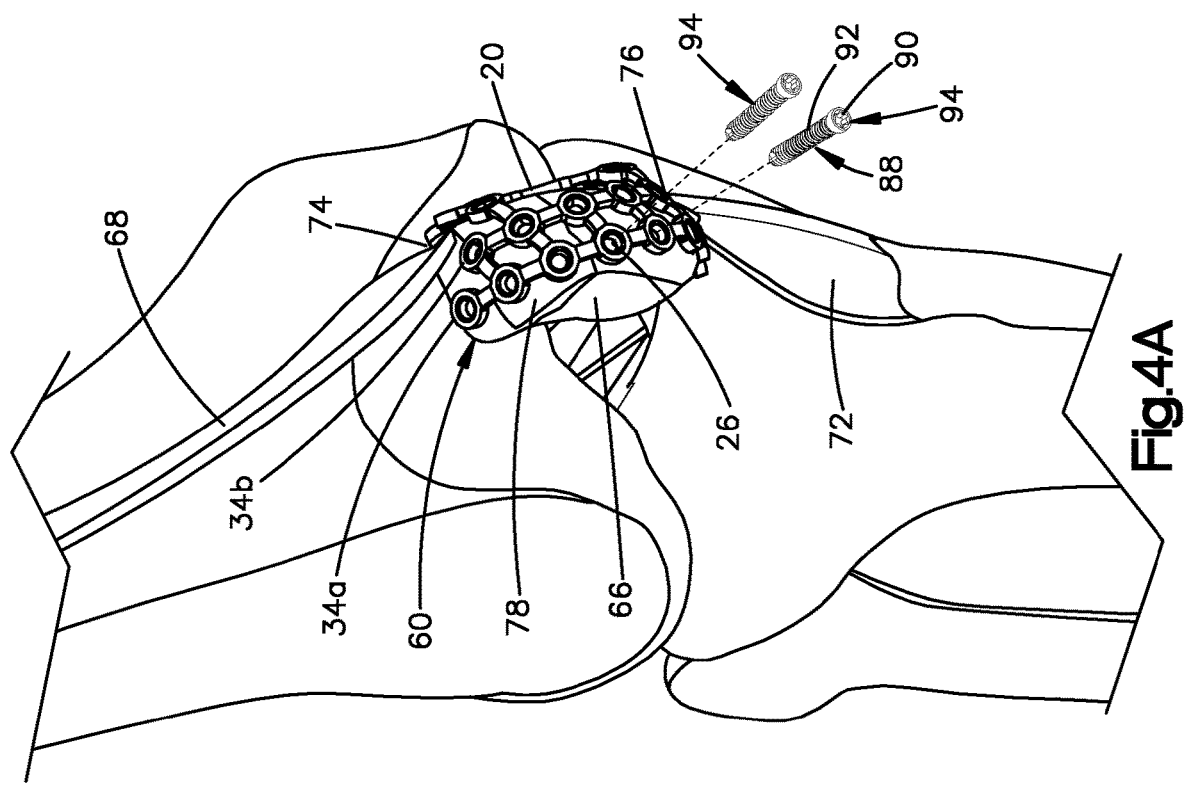
FIG. 4B is a schematic perspective view of the knee illustrated in FIG. 4A, showing the lateral fixation elements inserted through the bone plate and into the patella.
Figure 4C:
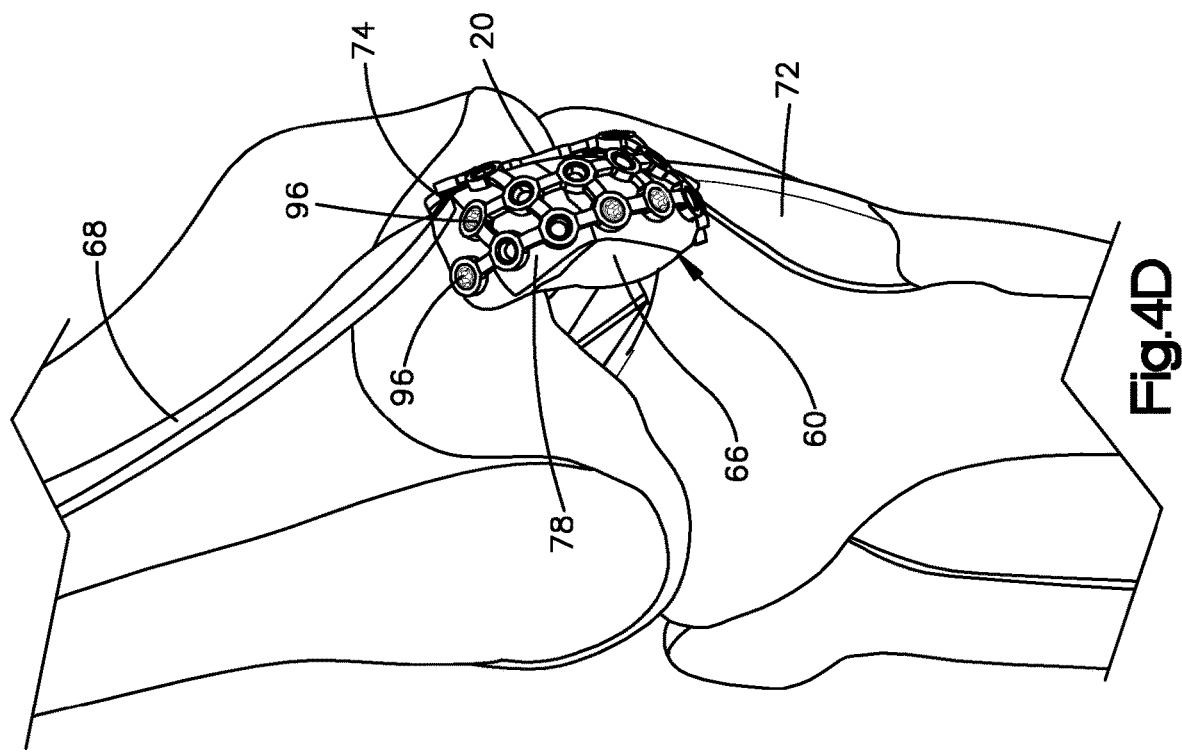
FIG. 4C is a schematic perspective view of the knee illustrated in FIG. 4B, showing a superior fixation element aligned for insertion through the bone plate and into the patella.
Figure 4D:
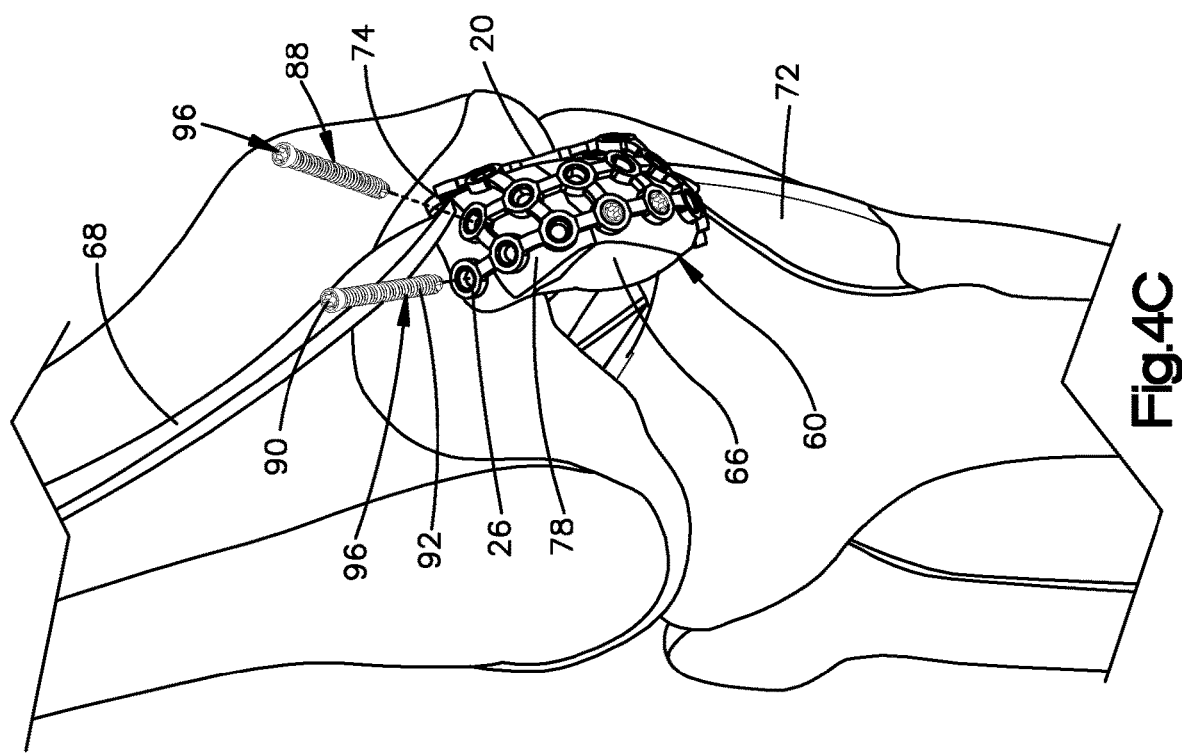
FIG. 4D is a schematic perspective view of the knee illustrated in FIG. 4B, showing the superior fixation element inserted through the bone plate and into the patella.
Figure 4H:
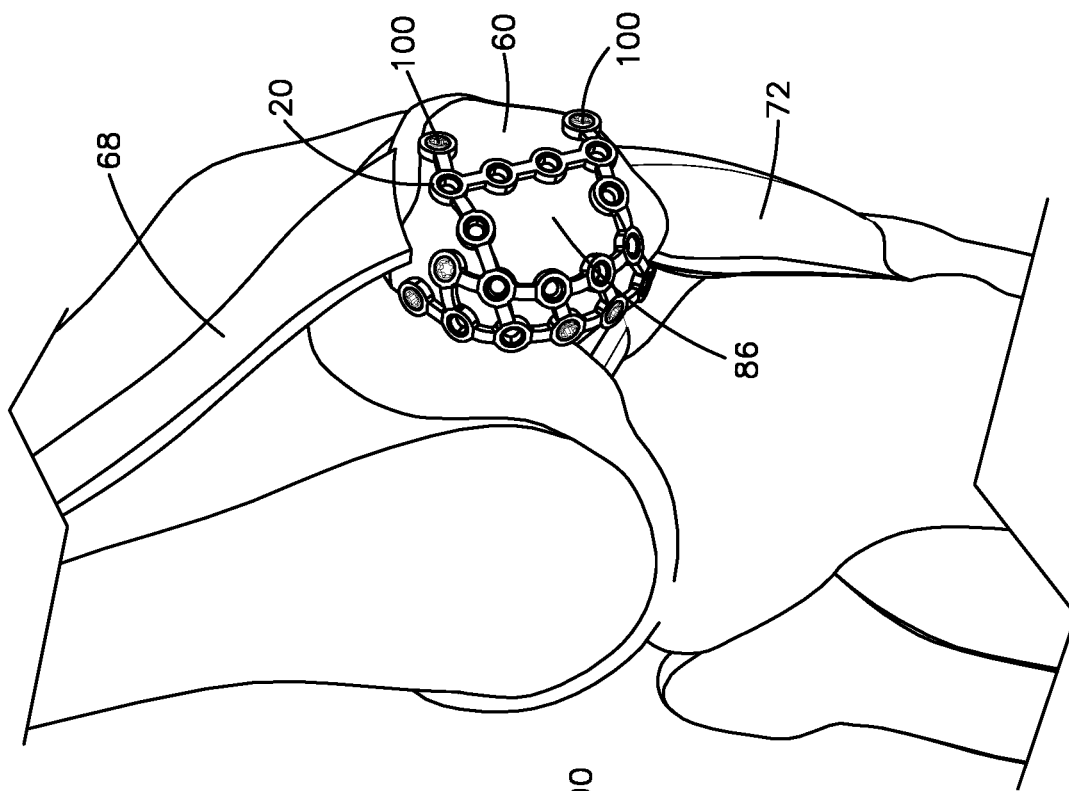
FIG. 4H is a schematic perspective view of the knee illustrated in FIG. 4G, shown with the anterior fixation elements inserted through the bone plate and into the patella.
Figure 4G:
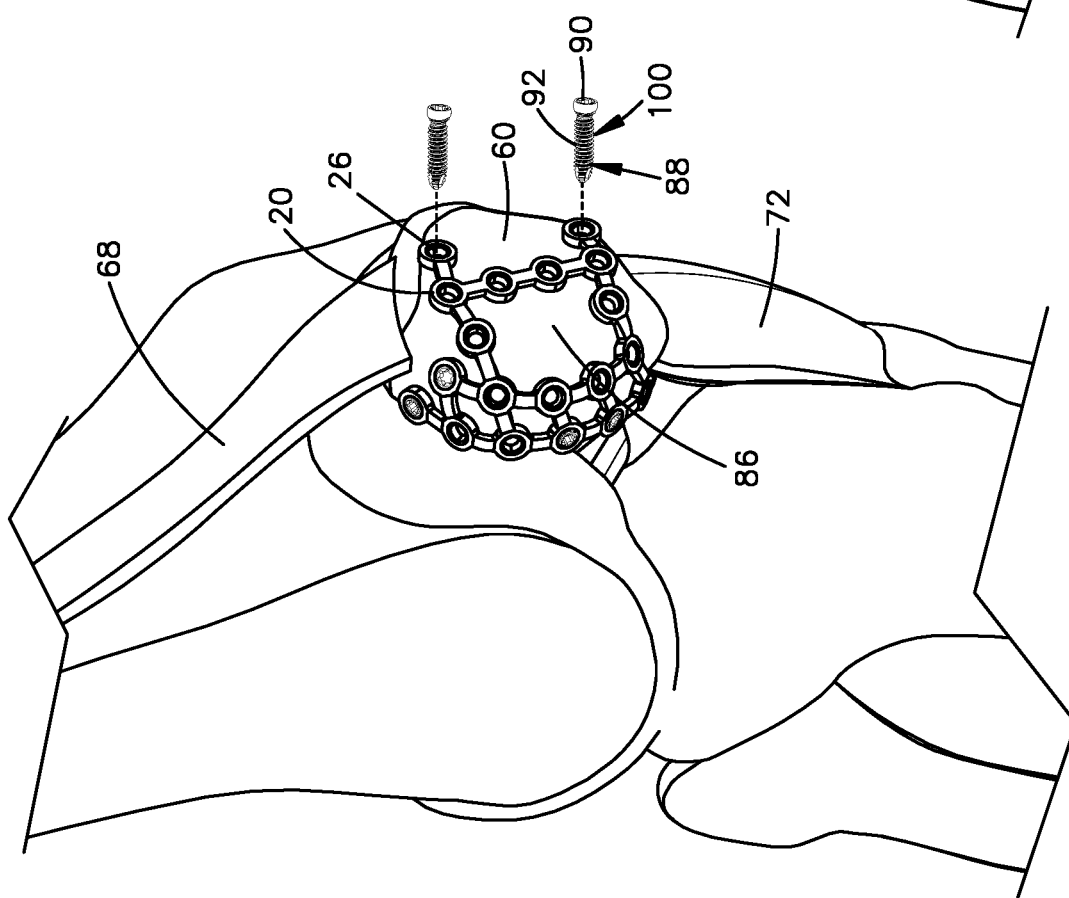
FIG. 4G is a schematic perspective view of the knee illustrated in FIG. 4F, showing a pair of anterior fixation elements aligned for insertion through the bone plate and into the patella.

Referring now to FIG. 3A, the patella 60 is an ovoid, triangular shape bone. The proximal roughly 75 percent of the patella 60 is composed of cortical-cancellous bone anteriorly with thick articular cartilage on the posterior surface. Distally near the inferior pole 76, the patella 60 is composed of thinner cancellous bone. The patella 60 defines an articular surface 66 (see FIG. 3B) that is mainly divided by the major vertical ridge into the lateral and medial facets, with the lateral facet typically being the larger of the two. The patella 60 lies in a subcutaneous position with strong fascial attachments that compose the quadriceps tendon 68 proximally (quadriceps tendon 68 shown only in FIG. 3A for the purpose of simplicity), the retinaculum medially and laterally, and the patellar tendon 72 distally. These soft tissue structures together with the patella 60 comprise the extensor mechanism. The quadriceps tendon 68 originates from the superior pole 74 and is formed from a blending of the insertions of the four quadriceps muscles: rectus femoris, vastus medialis, vastus lateralis, vastus intermedius. The patellar tendon originates from the inferior pole 76 and inserts on the tibia tubercle. The patella retinaculum is formed from portions of the deep investing fascia lata with the vastus medialis and vastus lateralis aponeurotic fibers. It travels along the medial and lateral aspect of the patella 60 to insert on the proximal tibia and functions to assist with knee extension.

Historically, the intraosseous blood supply to the patella 60 was thought to originate from two main arterial systems that are the midpatellar vessels and the polar vessels. The midpatellar vessels penetrate the middle third of the patella, and the polar vessels penetrate the patella apex. However, more recent studies have demonstrated that the largest intraosseous arterial supply to the patella 60 in fact enters at the inferior or distal pole 76 and predominantly enters inferomedially. In addition, a deep peripatellar anastomotic ring has also been found that provides arterial blood supply. Because conventional understandings of the locations of primary blood supply to the patella 60 were inaccurate, conventional bone plates based on these conventional understandings risked a resulting avascular necrosis. The present method of fixation can avoid disruption of both the predominate inferomedial vessel and the peripatellar ring in order to preserve perfusion following the patella fracture fixation.

Two main surgical approaches for patella fractures include a midline longitudinal approach and a lateral parapatellar approach. The midline longitudinal approach includes creating a midline vertical incision down to the level of the retinaculum. Medial and lateral tissue flaps are raised to expose the extent of the retinacular tears. The present inventors have recognized the midline longitudinal approach creates difficulty visualizing the articular surface. Accordingly, the method of fixation includes a lateral parapatellar approach. The lateral parapatellar approach is believed to limit disruption to the patella vascularity, which as described above has been found to be primarily inferomedial. Thus, the method of fixation can include the step of creating a longitudinal skin incision 75 along the lateral border of the patella. The step of creating the incision 75 can further include creating the incision over the lateral edge of the patella down to the avascular subfascial layer. In one example, and the incision 75 can be made from the tibial tubercle to a location superior of the superior pole of the patella. For instance, the incision 75 can be made to a location between one and three inches above the superior pole of the patella. A limited lateral tissue flap can be raised to gain access to the articular capsule of the knee. It is appreciated that the incision along the lateral border of the patella can minimize the size of the lateral soft tissue flap for the lateral parapatellar arthrotomy. Prior to creating the incision, the knee is typically placed into approximately 20-30 degrees of flexion.

Once the incision has been created, the method of fixation can include the step of performing a lateral parapatellar arthrotomy. The lateral parapatellar arthrotomy can originate from the tear in the lateral retinaculum that is commonly present in patella fractures. The arthrotomy allows for direct visualization of the articular surface 66, which significantly reduces the difficulty of obtaining an anatomic reduction compared to conventional techniques. In particular, as is described in more detail below, the access to the patella 60 through the lateral parapatellar arthrotomy can allow for angular manipulation of the patella to expose the articular surface and ensure continuity of the articular surface 66 after fracture reduction. Thus, the arthrotomy can allow for exposure and reduction of the articular fragments. Thus, the method can further include the step of directly visualizing the articular surface of the patella. The method can further include the step of exposing and reducing the articular fragments while directly visualizing the articular surface. Further, the direct visualization of the articular surface allows for visualization of the placement of the bone plate 20 on the patella 60 at locations that avoids interference with the articular surface. Thus, the method can further include the step of directly visualizing the articular surface while fixing the bone plate 20 to the patella 60. The method can further include the step of fixing the bone plate 20 to the patella 60 while avoiding the inferomedial vascularity to the patella. In particular, the bone plate 20 can be placed against the bone plate 20 without causing the pate 20 to lie against the inferomedial vascularity to the patella. Once the lateral parapatellar arthrotomy has been completed, the method can include the step of irrigating the fracture site of the patella. The method can also include the step of removing the fracture hematoma. The method can further include the step of visually inspecting the patella 60 for loose bodies.

Referring now to FIG. 3B, the method of fixation can include the step of reducing the at least one fracture or fractures of the patella 60. In particular, the reducing step can be performed after the arthrotomy has been completed. The patella 60 can be everted so as to expose the articular surface 66, such that the method can include the step of directly visualizing the articular surface 66. For instance, the patella can be angulated between 75 degrees and 180 degrees substantially about a superior-inferior axis to gain visual access to the articular surface 66, and in particular to gain access to the at least one fracture location or fracture locations of the articular surface 66. The angular manipulation of the patella can also allow for easy removal of hematomas at fracture locations of the articular surface 66. In one example, during bone plate fixation, the patella can be angulated less than 180 degrees so as to simultaneously allow for access to the lateral aspect of the peripheral rim 78 of the patella 60. Thus, the bone plate 20 can be fixed to a lateral aspect of the rim 78 while visualizing the articular surface to ensure integrity and continuity of the articular surface. At certain times during the surgical procedure, the patella 60 can be angulated more or less as desired so as to gain the desired visual access to the articular surface while allowing for fixation of the bone plate 20 to the patella 60.

In one example, the step of reducing the patella can include the step of driving Kirschner wires (K-wires) 79 into select ones of the patella bone fragments 80, and manipulating the K-wires to adjust the position of the bone fragment or fragments 80. The K-wires can have any suitable diameter as desired. In one example, the K-wires can have a diameter between and including 1.5 mm and 2 mm. Thus, the K-wires can be used as joysticks that can translate and angulate the bone fragments to thereby reduce the at least one fracture or fractures. Reduction can further be performed using interfragmentary small fragment compression screws that can adjoin small fragments of the patellar fracture to each other, and reduce the fragments. During reduction, the patella 60 can be angulated as described above so as to provide visual access to the articular surface. The angulation can provide both direct visualization of fracture fragments and direct visualization of the articular surface. If further exposure or inversion is desired, the arthrotomy can be extended superiorly with a cuff of quadriceps tendon left on the vastus lateral left for later repair. Thus, the method can include the step of angulating the patella, and directly visualizing both at least a portion up to all of the fracture fragments and the articular surface. Alternatively, the patella 60 can be angulated intermittently after completion of a reduction operation to inspect the articular surface, to therefore assess whether additional reduction is to be performed. The reduction can be performed until the articular surface is aligned and the extensor mechanism is restored.

Referring now to FIG. 3C, fracture can further be performed by capturing bone fragments 80 to be reduced between the arms 82 of reduction clamps 84, and bringing the arms together so as to thereby urge the captured bone fragments 80 toward each other. The reduction clamps 84 can be used alone or in combination with either or both of the K-wires 79 and interfragmentary small fragment compression screws. Similarly, the K-wires 79 can be used alone or in combination with either or both of the reduction clamps 84 and the interfragmentary small fragment compression screws.

In one example, the K-wires 79 alone or in combination with the interfragmentary small fragment compression screws can be used to reduce the at least one fracture or fractures, and the reduction clamps can hold the fracture fragments in their reduced state while the bone plate 20 is fixed to the patella 60. In one example, smaller fragments are held together with the threaded K-wires 79 alone or in combination with the interfragmentary small fragment compression screws so as to construct larger fragments that can then be reduced to one another under pressure provided by the reduction clamps. The bone plate 20 can then be applied to the patella 60. In this regard, it should be appreciated that the K-wires 79 should be driven into the respective bone fragments at locations that do not interfere with placement of the bone plate 20 onto the patella 60. Depending on the nature of the fracture, the reducing step can reduce fractures at the articular surface so as to achieve realignment and continuity of the articular surface.

Referring now to FIGS. 4A-4H generally, once the fractured patella 60 has been reduced, the bone plate 20 can be fixed to the patella 60. In FIGS. 4A-4H, the K-wires 79 and reduction clamps 84 are not shown in order to more clearly illustrate the bone plate 20, but it is appreciated that the K-wires 79 and reduction clamps 84 can remain in place until fixation of the bone plate 20 to the patella 60 has stabilized the reduced fragments, at which point the K-wires 79 and reduction clamps 84 can be removed.

After the patella 60 has been reduced, the method can include the step of inserting the bone plate 20 through the lateral parapatellar incision 75, and positioning the bone plate around at least a portion of the patella 60. For instance, the plate 20 can be positioned such that the inner surface 24a faces the patella 60. A first portion of the plate 20, which can be defined by the base 32, can face a lateral side of the peripheral rim 78. A second portion of the plate 20, which can be defined by the outer portion 40, can face the anterior surface 86 of the patella 60. A first end of the first portion, which can be defined by the first outer section 32b of the base 32, can face the superior pole 74 of the patella. A second end of the first portion, which can be defined by the second outer section 32c of the base 32, can face the inferior pole 76 of the patella 60. The plate 20 can be configured to be in alignment with the patella 60 beneath the patellar tendon and quadriceps tendon while also extending over the anterior wall of the patella 60. Thus, the plate 20 can span half or more of the perimeter of the patella. For instance, the bone plate can span a lateral half of the perimeter. As described above, the plate size can be selected based on patient size and the shape of the patella.

In particular, the plate 20 can be contoured to fit around the peripheral rim 78 of the reduced patella and the cortical anterior surface 86 of the patella 60. For instance, the bone plate 20 can be positioned such that the intermediate section 32a of the base 32 faces the lateral end of the peripheral rim 78 of the patella 60, and the outer portion 40 faces the anterior surface 86 of the patella 60. The first outer section 32b of the base 32 can define a first extension that faces the patella 60 at a location superior of the intermediate section 32a. For instance, the first outer section 32b of the base 32 can define a first extension that faces a bony surface of the superior patella at a location posterior of (beneath) the quadriceps tendon. The second outer section 32c of the base 32 can define a second extension that is configured to face the patella 60 at a location inferior of the intermediate section 32a. For instance, the second outer section 32c of the base 32 can define a second extension that faces the non-articulating distal pole of the patella 60 at a location posterior of (beneath) the patellar tendon. The plate 20 is fashioned to achieve fixation to the patella 60 at each major fracture fragment without encroachment on the quadriceps and patellar tendinous insertions on the superior and inferior pole of the patella 60. This avoids releasing the quadriceps and patellar, which can already be compromised by the injury that caused the patella fracture, from the patella 60. It is recognized that the shape and contour of the plate 20 can be modified to adapt to various different fracture patterns.

As described above a fixation system can include the bone plate 20 and a plurality of fixation elements 88. The fixation element 88 can include a head 90 and a shaft 92 that extends out with respect to the head 90. At least a portion of the shaft 92 can be threaded. For instance, an entirety of the shaft can be threaded. In another example, the fixation element can be configured as a lag screw wherein the distal end of the shaft 92 is threaded, but the shaft remains unthreaded between the head and the threaded distal end. The shaft 92 can have a length sufficient so as to extend through a cortical wall of the rim 78 at a first location, extend through the patella, and be embedded in a cortical wall of the rim at a second location. The second location can be substantially opposite the first location. Thus, in one example, the shaft 92 can have a length sufficient so as to extend through the lateral side of the rim 78, extend through the patella 60, and embed in the cortical wall at the medial side of the rim 78. In another example, the shaft 92 can have a length sufficient so as to extend through the proximal pole of the rim 78, through the patella 60, and embed in the cortical wall at the superior pole of the rim 78. In this regard, the fixation element 88 can be referred to as a bicortical screw. Alternatively, the shaft 92 can be configured as a unicortical screw whose shaft has a length suitable to threadedly purchase with the cortical wall at the location of the bone through which the fixation element 88 extends. The fixation elements 88 can include shafts 92 having different diameters. For instance, while certain ones of the shafts can have a diameter of 2.4 mm and certain others of the shafts can have a diameter of 2.7 mm are envisioned, shafts of any suitable alternative diameter are contemplated by the present disclosure.

Further, one or more of the fixation elements 88 can be configured as compression screws. In particular, at least one or both of the external surface of the head 90 and the internal surface of the eyelet 28 that defines the fixation hole 26 can be unthreaded. Accordingly, as the head 90 is brought into the fixation hole 26 while the shaft is driven into the patella 60, the head 90 is configured to compress the bone plate 20 against the patella 60 as the shaft 92 is driven into bone. In other examples described below (see FIG. 4G), one or more of the fixation elements 88 can be configured as a locking screw, whereby the external surface of the head 90 is threaded. Further, the internal surface of the eyelet 28 that defines the fixation hole 26 can also be threaded. Thus, as the head 90 is brought into the fixation hole 26 while the shaft is driven into the patella 60, the head 90 is configured to threadedly mate with the bone plate 20 in the fixation hole 26. While certain steps of fixing the bone plate 20 to the patella 60 are described in connection with certain types of fixation elements, it should be appreciated that the disclosure is not limited to the particular type of fixation element described, and that any suitable alternative type of fixation element could instead be used as desired. Further, the number of fixation elements inserted through the bone plate 20 and into the patella 60, and size of screws can often be determined by fracture pattern and bone quality of the patella 60.

Referring now to FIGS. 1A-2C and 4A-4B, after the plate 20 has been positioned around the patella 60, at least one first or lateral fixation element 94 of the plurality of fixation elements 88 can be driven through one of the fixation holes 26 of the eyelets 28 in a lateral-to-medial direction. The at least one lateral fixation element 94 can thus be configured to achieve initial fixation of the plate 20 to the patella 60.

Fixation of the bone plate 20 to the patella with the at least one lateral fixation element 94 can achieve stable compression and absolute stability of the major fracture fragments.

The at least one lateral fixation element 94 can be configured as a bicortical compression screw, though as described above any one or more up to all of the at least one lateral fixation element 94 can be configured as any suitable type of alternative fixation element as described above. In one example, the lateral fixation element 94 can be driven through one of the fixation holes 26 of the intermediate section 32*a* and at least into the lateral aspect of the rim 78. The threaded shaft 92 can threadedly purchase with cortical bone at the anterior aspect of the rim 78. Further, the lateral fixation element 94 can be driven into the reduced patella 60 until the threaded shaft 92 extends across the patella 60 and can threadedly purchase in cortical bone on the medial side of the patella 60.

The at least one lateral fixation element 94 can include a plurality of lateral fixation elements 94 that can be driven into respective fixation holes 26 of the intermediate section 32*a*. While a pair of lateral fixation elements 94 are shown, any suitable number of fixation elements 88 can be driven through the respective fixation holes 26 of the intermediate section 32*a* into the patella 60, with care taken so that the fixation elements 88 inserted through the intermediate section 32*a* do not interfere with insertion of other fixation elements 88 to be inserted through other locations of the bone plate 20 and into the patella. The lateral fixation elements 94 can be inserted into different ones of the first and second rows 34*a* and 34*b*, or can be inserted into the same row as desired. For instance, the at least one lateral fixation element 94 can be driven through a bone fixation hole 26 defined by the middle segment 37*c* of the first row 34*a*. Alternatively or additionally, the at least one lateral fixation element 94 can be driven through a bone fixation hole 26 defined by the middle segment 38*b* of the second row 34*b*. The lateral fixation elements 94 can, for instance, be driven in the medial direction into the superior and inferior poles of the patella 60 to seat the plate 20 against the patella 60. It should also be appreciated that the bicortical fixation of the plate 20 to the patella 60 in the lateral-to-medial direction can be multiplanar.

Referring now to FIGS. 4C-4H generally, after initial fixation of the plate 20 to the patella 60, the contour of the plate 20 with respect to the patella 60 can be inspected, and additional contouring of at least one or more up to all of the first and second outer sections 32*b* and 32*c* of the base, and the first and second columns 42*a* and 42*b* can be performed. Advantageously, the plate 20 can achieve the fixation described herein without overlapping the articular surface of the patella. The contouring of the first and second columns 42*a* and 42*b* can also achieve a low profile of the plate 20 on the anterior surface 86 of the patella 60.

Referring to FIGS. 1A-2C and 4C-4D, at least one second or superior fixation element 96 can be driven through the plate 20 and into the patella 60 in the distal (or superior-to-inferior) direction so as to thereby fix a superior end of the plate 20 to the patella 60. In particular, the at least one superior fixation element 96 can be driven through a respective at least one of the bone fixation holes 26 of the first outer section 32*b* of the base 32 and into a bony surface of the patella 60 at the superior or proximal end of the patella 60. For example, the at least one superior fixation element 96 can be driven through the peripheral rim 78 of the patella 60 at the superior pole of the patella 60. Because the first outer section 32*b* of the base 32 is disposed posterior of the quadriceps tendon, the at least one superior fixation element 96 can likewise be driven through the plate 20 and into the patella 60 at a location posterior of the quadriceps tendon. Thus, it can be said that the at least one superior fixation element 96 can be driven through an extension of the bone plate 20 that is disposed against a bony surface of the superior patella at a location posterior of the quadriceps tendon. The at least one fixation hole 26 that receives the at least one superior fixation element 96 can be an inferior-most hole 26 of the bone plate 20, though it should be appreciated that any fixation hole 26 of the plate 20 aligned with the superior end of the patella 60 can be used.

In one example the at least one superior bone fixation element 96 can be driven through a bone fixation hole 26 defined by the first longitudinal end 37*a* of the first row 34*a*. Alternatively or additionally, the at least one superior bone fixation element 96 can be driven through a bone fixation hole 26 defined by the first longitudinal end 38*a* of the second row 34*b*.

The at least one superior fixation element 96 can be configured as a bicortical compression screw, though as described above one or more up to all of the at least one superior fixation element 96 can be configured as any suitable alternative type of fixation element described above. For instance, the at least one superior fixation element 96 can be configured as a unicortical compression screw. In one example, the at least one superior fixation element 96 can be driven through one of the fixation holes 26 of the first outer section 32*b* and at least into the superior aspect of the rim 78. The threaded shaft 92 can threadedly purchase with cortical bone at the superior end of the patella. Further, the at least one superior fixation element 96 can be driven into the reduced patella 60 until the threaded shaft 92 extends across the patella 60 and can threadedly purchase in cortical bone at the inferior end of the patella 60.

Alternatively, if the at least one superior fixation element 96 is a unicortical screw, the shaft 92 threadedly purchases with the cortical wall at the superior end of the patella 60, but does not extend across the patella 60 a sufficient distance so as to threadedly purchase with the cortical wall at the inferior end of the patella 60. It is recognized that the superior end of the patella 60 has dense bone that can be suitable for reliable threaded purchase by the at least one superior fixation element 96, and thus the superior fixation element 96 can be a unicortical fixation element.

Because the at least one superior fixation element 96 can be a compression screw, the head 90 of the at least one superior fixation element 96 can compress the plate 20 against the superior end of the patella 60 at a location posterior of the quadriceps tendon. Any number of superior fixation elements 96 can be driven through respective fixation holes 26 of the plate 20 and into the patella 60 so as to provide fixation of the plate 20 to the patella as desired. For instance, the fixation of the plate 20 to the superior end of the patella 60 can occur along more than one plane, thereby enhancing fixation.

Referring now to FIGS. 1A-2C and 4E-4F, at least one third or inferior fixation element 98 can be driven through the plate 20 and into the patella 60 in the proximal (or inferior-to-superior) direction so as to thereby fix an inferior end of the plate 20 to the patella 60. In particular, the at least one inferior fixation element 98 can be driven through a respective at least one of the bone fixation holes 26 of the second outer section 32*c* of the base 32 and into a bony surface of the patella 60 at the inferior or distal end of the patella 60. For example, the at least one inferior fixation element 98 can be driven through the peripheral rim 78 of the patella 60 at the inferior pole of the patella 60. In particular, the at least one inferior fixation element 98 can be driven into the non-articulating inferior pole of the patella 60. Because the second outer section 32c of the base 32 is disposed posterior of the patellar tendon, the at least one inferior fixation element 98 can likewise be driven through the plate 20 and into the patella 60 at a location posterior of the patellar tendon. Thus, it can be said that the at least one inferior fixation element 98 can be driven through an extension of the bone plate 20 that is disposed against a bony surface of the inferior end of the patella 60 at a location posterior of the patellar tendon. The at least one fixation hole 26 that receives the at least one inferior fixation element 98 can be an inferior-most hole 26 of the bone plate 20, though it should be appreciated that any fixation hole 26 of the plate 20 aligned with the inferior end of the patella 60 can be used In one example the at least one inferior bone fixation element 98 can be driven through a bone fixation hole 26 defined by the second longitudinal end 37b of the first row 34a. Alternatively or additionally, the at least one superior bone fixation element 98 can be driven through a bone fixation hole 26 defined by a second longitudinal end of the second row 34b in examples where the second row 34b includes a second longitudinal end.

It should be appreciated that the at least one second or superior fixation element 96 can be driven antegrade through the plate 20 in the distal direction, and the at least one third or inferior fixation element 98 can be driven retrograde through the plate 20 in the proximal direction, thereby provide interfragmentary compression across the fracture fragments of the patella 60 and correspondingly achieving stability of the fracture.

The present disclosure recognizes that the inferior pole of the patella 60 can be more osteoporotic than the superior pole of the patella 60. Further, the fracture of the patella at the inferior pole can be more comminuted than at the superior pole. Accordingly, the at least one inferior fixation element 98 can be configured as a locking screw. Further, the at least one inferior fixation element 98 can be configured as a bicortical screw. It should be appreciated, however, as described above that one or more up to all of the at least one inferior fixation element 98 can be configured as any suitable alternative type of fixation element described above. In one example, the at least one inferior fixation element 98 can be driven through one of the fixation holes 26 of the second outer section 32b and at least into the inferior pole of the patella 60. The threaded shaft 92 can threadedly purchase with cortical bone at the inferior pole. Further, the at least one inferior fixation element 98 can be driven into the reduced patella 60 until the threaded shaft 92 extends across the patella 60 and can threadedly purchase in cortical bone at the superior end of the patella 60. As described above, the cortical bone at the superior end of the patella 60 is often more dense and strong than the cortical bone at the inferior end of the patella 60. Accordingly, because the at least one inferior fixation element 98 can be bicortical, the at least one inferior fixation element 98 can reliably threadedly purchase with strong dense bone.

Because the at least one inferior fixation element 98 can be a locking screw, the head 90 of the at least one inferior fixation element 98 can threadedly mate with the plate 20 inside the fixation hole 26. Thus, the fixation holes 26 at the second outer section 32c of the base 32 can be configured as internally threaded locking holes. Because the at least one inferior fixation element 98 can be configured as a locking screw, the head 90 does not compress the plate against the patella 60 when the at least one inferior fixation element 98 is fully seated in the bone plate 20 and bicortically secured to the patella 60. Any number of inferior fixation elements 98 can be driven through respective fixation holes 26 of the plate 20 and into the patella 60 so as to provide fixation of the plate 20 to the patella 60 as desired. For instance, the fixation of the plate 20 to the inferior end of the patella 60 can occur along more than one plane, thereby enhancing fixation.

Referring now to FIGS. 1A-2C and 4G-4H, at least one fourth or anterior fixation element 100 can be driven posteriorly through an anterior portion of the plate 20 into the anterior wall of the patella 60 that is opposite the articular surface 66. The anterior wall defines the anterior surface 86. As described above, the anterior portion of the plate 20 can be defined by the outer portion 40. Thus, the at least one anterior fixation element 100 can be driven through a respective at least one fixation hole of the outer portion 40 of the bone plate 20 so as to fix the plate 20 to the anterior surface 86 of the patella 60. In particular, the at least one anterior fixation element 100 can be driven through a respective at least one hole of the first column 42a, the second column 42b, or each of the first and second columns 42a and 42b. As described above, the anterior, superior, and inferior fixation elements can achieve multiplanar fixation of the bone plate 20 to the patella 60. Fixation of the anterior portion of the plate 20 to the patella 60 provides an additional plane of fixation so as to further stabilize comminuted patella fractures, and to allow for fixation in the anteroposterior direction.

The at least one anterior fixation element 100 can be configured as a locking screw or a compression screw. Accordingly, the anterior fixation element 100 is driven posteriorly through the fixation holes 26 of the anterior portion of the plate 20 until fully seated in the plate 20. If the anterior fixation element 100 is a compression screw, then the head 90 of the anterior fixation element 100 can compress the plate 20 against the anterior surface 86 of the patella 60. Alternatively, if the anterior fixation element 100 is a locking screw, then the head 90 of the anterior fixation element 100 can threadedly purchase with a threaded locking hole 26 of the plate 20 at the anterior portion of the plate 20.

Further, the at least one anterior fixation element 100 can be configured as a unicortical screw. Accordingly, when the at least one anterior fixation element 100 is fully seated in the respective at least one fixation hole 26, the shaft 92 terminates anterior of the cortical bone at the anterior wall of the patella 60. As a result, the shaft 92 can be configured so as to not interfere with the continuity of the articular surface 66. Direct visualization of the articular surface achieved by the angulation of the patella 60, as well as anteroposterior and lateral fluoroscopy, can be used to ensure that at least one anterior fixation element 100 has not violated the articular surface 66. It is recognized that the at least one anterior fixation element 100 can include a single anterior fixation element 100 that is fixed to the plate 20 and the patella 60 through a respective fixation hole 26, or a plurality of anterior fixation elements 100 fixed to the plate 20 and the patella 60 through a respective plurality of fixation holes 26. For instance a first one of the plurality of anterior fixation elements 100 can be driven through the first column 42a, and a second one of the plurality of anterior fixation elements 100 can be driven through the second column 42b. In one example, a first one of the plurality of anterior fixation elements 100 can be driven through the second lateral end 46b of the first column 42a. A second one of the plurality of anterior fixation elements 100 can be driven through the second lateral end 48*b* of the second column 42*b*.

While the at least one superior fixation element 96 is described as being driven through the plate 20 and into the patella 60 prior to driving the at least one inferior fixation element 98 through the plate 20 and into the patella 60, and the at least one inferior fixation element 98 is described as being driven through the plate 20 and into the patella 60 prior to driving the at least one anterior fixation element 100 through the plate 20 and into the patella 60, fixation of the plate 20 to the patella 60 can occur in any order as desired. For instance, the at least one inferior fixation element 98 can be driven through the plate 20 and into the patella 60 prior to driving the at least one superior fixation element 96 through the plate 20 and into the patella 60. It should be appreciated that the steps of fixing the plate 20 to the patella 60 allows fixation of each fragment of the patella 60, for instance in situations where large pieces of articular comminution exist.

Referring now to FIGS. 1A-2C and 5, it is recognized that the inferior pole 76 of the patella 60 can often be comminuted, and can contain osteoporotic bone. In fact, inferior pole comminution has been observed in 88% of fractures of the patella 60. Accordingly, fixation of the bone plate 20 to the patella 60 can be augmented by suture fixation. The method of fixation can further include the step of augmenting fixation of the plate 20 to the patella 60 by fixing at least one suture to the patellar tendon 72 and to the plate 20. In one example, the sutures can be configured as FiberWire® sutures commercially available from Arthrex, having a place of business in Naples, Fla., though it should be appreciated that any suitable suture is envisioned. Thus, the method can include the step of attaching one or more sutures 102 to the patellar tendon 72. The sutures 102 can thus be included in the fixation system. In one example, the sutures 102 can be passed beneath the anterior portion of the plate 20, between the plate 20 and the patella 60, and medially and laterally through the patellar tendon 72 in a Krackow configuration. The free end of the suture 102 can then be passed over the plate in the inferior direction, and tied to the plate 20. For instance, the sutures 102 can be tied to at least one of the links 30 of the bone plate 20. In one example, the sutures 102 can be passed through the fixation holes 26 of the anterior portion of the plate 20 and subsequently tied to the plate 20. The fixation holes 26 can be defined by the second column 42*b*. Thus, the suture 102 can further anchor the bone plate 20 to the patellar tendon 72, which enhances the stability of the bone plate 20 at the inferior pole 76. It is thus appreciated that the suture 102 can augmenting It is desirable for the knee to be in extension during the suture fixation. The retinacular tears can be repaired with any suitable suture in a figure-eight pattern. The suture used for repairing retinacular tears can, for example, be a #2 Ethibond® suture commercially available from Ethicon, having a place of business in Somerville, N.Y., or #2 Fiberwire® sutures.

It should be noted that the illustrations and discussions of the embodiments shown in the figures are for exemplary purposes only, and should not be construed limiting the disclosure. One skilled in the art will appreciate that the present disclosure contemplates various embodiments. Additionally, it should be understood that the concepts described above with the above-described embodiments may be employed alone or in combination with any of the other embodiments described above. It should further be appreciated that the various alternative embodiments described above with respect to one illustrated embodiment can apply to all embodiments as described herein, unless otherwise indicated.

What is claimed:

1. A method of treating a fractured patella, the method comprising the steps of:
   creating a longitudinal skin incision along a lateral border of the patella;
   inserting a bone plate through the incision and around at least a portion of the patella, such that 1) first and second parallel rows of bone fixation holes of a base of the bone plate face a lateral portion of a circumferential rim of the patella, an inferior pole of the patella, and a superior pole of the patella, and 2) an outer portion of the bone plate that extends from the base faces an anterior surface of the patella;
   driving a lateral fixation element through the bone plate into the circumferential rim substantially along a medial direction;
   driving second fixation elements through the bone plate and into respective ones of the inferior pole and the superior pole; and
   driving an anterior fixation element through the outer portion and into the anterior surface of the patella.

2. The method as recited in claim 1, further comprising, after the creating step and before the inserting step, the step of performing a lateral parapatellar arthrotomy.

3. The method as recited in claim 2, further comprising the step of angulating the patella so as to gain direct visual access of an articular surface of the patella.

4. The method as recited in claim 3, wherein the step of angulating is performed prior to the step of driving the lateral fixation element.

5. The method as recited in claim 3, wherein the step of driving the second fixation elements comprises the step of driving at least one superior fixation element of the second fixation elements through the bone plate and into the superior pole of the patella in a superior-to-inferior direction, so as to fix the bone plate to the superior pole.

6. The method as recited in claim 5, wherein the step of driving the at least one superior fixation element compresses the bone plate against the superior pole of the patella, and further causes the at least one superior fixation element to threadedly purchase with cortical bone at the superior pole.

7. The method as recited in claim 5, wherein the step of driving the second fixation elements further comprises the step of driving at least one inferior fixation element of the second fixation elements through the bone plate and into the inferior pole of the patella in an inferior-to-superior direction, so as to fix the bone plate to the inferior pole.

8. The method as recited in claim 7, wherein the step of driving the at least one inferior fixation element further comprises threadedly purchasing the at least one inferior fixation element in cortical bone of the superior pole.

9. The method as recited in claim 7, wherein the step of driving the at least one inferior fixation element comprises the step of threadedly mating a head of the at least one inferior fixation element to the plate.

10. The method as recited in claim 7, further comprising the step of directly visually inspecting the articular surface during at least one of the driving steps.

11. The method as recited in claim 7, further comprising the step of passing at least one suture between the second portion of the plate and the patella, switching the suture into a patellar tendon that is attached to the patella, and attaching the at least one suture to the bone plate.

12. The method as recited in claim 1, wherein the driving steps comprise driving the lateral fixation element through a first eyelet that defines a first bone fixation hole of the bone plate, and driving the second fixation elements through respective second eyelets that define respective second bone fixation holes of the bone plate.

13. The method as recited in claim 12, wherein the driving steps comprise threadedly purchasing the lateral fixation element with the bone plate in the first bone fixation hole, and threadedly purchasing the second fixation elements with the bone plate in the respective second bone fixation holes.

14. The method as recited in claim 12, wherein the first and second bone fixation holes are unthreaded.

15. The method as recited in claim 1, wherein the bone plate comprises:
   a bone plate body defining an inner surface configured to face the patella, and an outer surface opposite the inner surface, the bone plate body including:
   i) the first row having an intermediate section that is fixed to the lateral portion of a circumferential rim of the patella, a first outer section that extends substantially along a first select longitudinal direction from the intermediate section and is fixed to the superior pole of the patella, and a second outer section that extends from the intermediate section substantially along a second select longitudinal direction opposite the first select longitudinal direction and is fixed to the inferior pole of the patella, and the second row is spaced from the first row and disposed adjacent the first row along a first select lateral direction that is substantially perpendicular to a longitudinal direction that includes each of the first and second select longitudinal directions, wherein the second row extends in the longitudinal direction; and
   ii) the outer portion that extends from the base along the first select lateral direction,
   wherein each of the intermediate section, the first outer section, the second outer section, the second row, and the outer portion defines a respective at least one bone fixation hole, the first outer section defines a first bone fixation hole that is disposed outward with respect to all bone fixation holes of the second row along the first select longitudinal direction, and the second outer section defines a second bone fixation hole that is disposed outward with respect to all bone fixation holes of the second row along the second select longitudinal direction, wherein 1) all bone fixation holes of the first row are inline with each other along the longitudinal direction, and 2) each bone fixation hole extends through the bone plate body from the outer surface to the inner surface, and
   wherein the first row is an outermost row of the bone plate with respect to a second select lateral direction that is opposite the first select lateral direction.

* * * * *